US011602739B2

(12) United States Patent
Xu et al.

(10) Patent No.: US 11,602,739 B2
(45) Date of Patent: Mar. 14, 2023

(54) CATALYSTS, METHODS OF MAKING, AND METHODS OF HYDROFLUORINATION

(71) Applicant: UNIVERSITY OF LOUISVILLE RESEARCH FOUNDATION, INC., Louisville, KY (US)

(72) Inventors: Bo Xu, Louisville, KY (US); Zhichao Lu, Louisville, KY (US); Gerald B. Hammond, Shelbyville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 4 days.

(21) Appl. No.: 17/259,282

(22) PCT Filed: Jul. 22, 2019

(86) PCT No.: PCT/US2019/042770
§ 371 (c)(1),
(2) Date: Jan. 11, 2021

(87) PCT Pub. No.: WO2020/023354
PCT Pub. Date: Jan. 30, 2020

(65) Prior Publication Data
US 2021/0275998 A1 Sep. 9, 2021

Related U.S. Application Data

(60) Provisional application No. 62/775,718, filed on Dec. 5, 2018, provisional application No. 62/702,173, filed on Jul. 23, 2018.

(51) Int. Cl.
*B01J 31/08* (2006.01)
*B01J 37/26* (2006.01)
*B01J 37/30* (2006.01)
*B01J 41/04* (2017.01)
*B01J 41/12* (2017.01)
*B01J 47/02* (2017.01)
*C07B 39/00* (2006.01)
*C07C 67/287* (2006.01)
*C07C 209/74* (2006.01)
*C07D 213/803* (2006.01)
*C07D 309/08* (2006.01)

(52) U.S. Cl.
CPC ............. *B01J 31/08* (2013.01); *B01J 37/26* (2013.01); *B01J 37/30* (2013.01); *B01J 41/04* (2013.01); *B01J 41/12* (2013.01); *B01J 47/02* (2013.01); *C07B 39/00* (2013.01); *C07C 67/287* (2013.01); *C07C 209/74* (2013.01); *C07D 213/803* (2013.01); *C07D 309/08* (2013.01); *B01J 2231/32* (2013.01); *B01J 2231/34* (2013.01); *B01J 2231/48* (2013.01)

(58) Field of Classification Search
CPC .. B01J 31/08; B01J 31/10; B01J 37/30; C07B 39/00; C07C 67/287; C07C 209/74; C07D 213/803; C07D 309/08
See application file for complete search history.

(56) References Cited

U.S. PATENT DOCUMENTS

| 2013/0274357 A1* | 10/2013 | SenGupta | B01J 20/06 521/26 |
|---|---|---|---|
| 2016/0187305 A1* | 6/2016 | Srinivasan | B01D 15/08 210/85 |
| 2016/0354770 A1* | 12/2016 | Murray | B01J 41/14 |
| 2018/0273401 A1* | 9/2018 | SenGupta | B01J 39/07 |
| 2019/0291094 A1* | 9/2019 | Saini | B01J 41/13 |

FOREIGN PATENT DOCUMENTS

EP 3960777 A1 * 3/2022

OTHER PUBLICATIONS

Z. Lu et al., 21 Green Chemistry, 2224-2228 (Dec. 26, 2018) (Year: 2018).*
S. Colonna et al., J. Chem. Soc., Perkin Trans. I, 2248-2252 (1979) (Year: 1979).*
International Search Report from PCT/US2019/042770, dated Oct. 25, 2019, 3 pages.
Written Opinion from PCT/US2019/042770, dated Oct. 25, 2019, 6 pages.
Alder et al. (2002) "Aromatic 4-Tetrahydropyranyl and 4-Quinuclidinyl Cations. Linking Prins with Cope and Grob" J Am Chem Soc, vol. 124, No. 18, pp. 4960-4961.
Amii et al. (2013) "Flow microreactor synthesis in organo-fluorine chemistry" Beilstein J. Org. Chem, vol. 9, pp. 2793-2802.
Arundale et al. (1952) "The Olefin-Aldehyde Condensation. The Prins Reaction." Chem Rev, vol. 51, No. 3, pp. 505-555.
Bondalapati et al. (2010) "Titanium tetrafluoride: An efficient Lewis acid and fluorinating agent for stereoselective synthesis of 4-fluorotetrahydropyran" J Fluorine Chem, vol. 131, No. 3, pp. 320-324.
Bucsi et al. (2002) "Stable Dialkyl Ether/Poly(Hydrogen Fluoride) Complexes: Dimethyl Ether/Poly(Hydrogen Fluoride), A New, Convenient, and Effective Fluorinating Agent1a" J Am Chem Soc, vol. 124, No. 26, pp. 7728-7736.

(Continued)

Primary Examiner — Alexander R Pagano
(74) Attorney, Agent, or Firm — ALGM LLP; Harry J. Guttman

(57) ABSTRACT

Some embodiments of the invention include inventive catalysts (e.g., catalysts of Formula (I)). Other embodiments include compositions comprising the inventive catalysts. Some embodiments include methods of using the inventive catalysts (e.g., in hydrofluorination of an organic compound). Further embodiments include methods for making the inventive catalysts. Additional embodiments of the invention are also discussed herein.

29 Claims, 6 Drawing Sheets

(56) References Cited

OTHER PUBLICATIONS

Campbell et al. (2015) "Modern Carbon-Fluorine Bond Forming Reactions for Aryl Fluoride Synthesis" Chem Rev, vol. 115, No. 2, pp. 612-633.
Cantillo et al. (2017) "Halogenation of organic compounds using continuous flow and microreactor technology" React Chem Eng, vol. 2, pp. 7-19.
Chambers (2004) "Fluorine in organic chemistry" Rev. and updated ed. Blackwell Pub./CRC Press, Oxford, Boca Raton, FL. (420 pages).
Champagne et al. (2015) "Monofluorination of Organic Compounds: 10 Years of Innovation" Chem Rev, vol. 115, No. 17, pp. 9073-9174.
Damera et al. (2015) "Stereoselective Synthesis of 1-Methyl-3',4',5',6'-tetrahydrospiro[indoline-3,2'-pyran]-2-one Derivatives via Prins Cyclization" J Org Chem, vol. 80, No. 11, pp. 5457-5463.
Fan et al. (2004) "Facile Preparation of β-Fluoro Amines by the Reaction of Aziridines with Potassium Fluoride Dihydrate in the Presence of Bu4NHSO4" J Org Chem, vol. 69, No. 2, pp. 335-338.
Gillis et al. (2015) "Applications of Fluorine in Medicinal Chemistry" J Med Chem, vol. 58, No. 21, pp. 8315-8359.
Gregorčič et al (1984) "Chemistry of organo halogenic molecules, LXXV. Polymer-supported hydrogen fluoride" J. Fluorine Chem, vol. 24, pp. 291-302.
Haufe (1996) "Triethylamine Trishydrofluoride in Synthesis" J Prakt Chem, vol. 338, No. 1, pp. 99-113.
Jaber et al. (2001) "Stereoselectivity and Regioselectivity in the Segment-Coupling Prins Cyclization" J Org Chem, vol. 66, No. 13, pp. 4679-4686.
Jasti et al. (2004) "Axial-Selective Prins Cyclizations by Solvolysis of α-Bromo Ethers" J Am Chem Soc, vol. 126, No. 32, pp. 9904-9905.
Kirk (2008) "Fluorination in Medicinal Chemistry: Methods, Strategies, and Recent Developments" Org Process Res Dev, vol. 12, No. 2, pp. 305-321.
Kirsch (2013) "Modern fluoroorganic chemistry: synthesis, reactivity, applications" Second, completely revised, and enlarged edition. Wiley-VCH, Verlag GmbH & Co. KGaA, Weinheim, Germany; Table of Contents and sections 1.1 to 1.4.3.2 (40 pages).
Launay et al. (2010) "Prins fluorination cyclisations: Preparation of 4-fluoro-pyran and -piperidine heterocycles" Bellstein J Org Chem, vol. 6, No. 41, (6 pages).
Lu et al. (2017) "Widely Applicable Hydrofluorination of Alkenes via Bifunctional Activation of Hydrogen Fluoride" J Am Chem Soc, vol. 139, No. 50, pp. 18202-18205.
Lu et al. (2019) "Multifaceted ion exchange resinsupported hydrogen fluoride: a path to flow hydrofluorination" Green Chemistry, vol. 21, No. 9, pp. 2224-2228 and Supporting Information.
Maeda et al. (1987) "Bromofluorination of double bonds using N-bromoimides and tetra-N-butylammonium fluoride as a source of floride" J Fluorine Chem, vol. 34, pp. 337-346.
McInnes et al. (2019) "Potential Diagnostic Imaging of Alzheimer's Disease with Copper 64 Complexes That Bind to Amyloid-β Plaques" Inorg Chem, vol. 58, No. 5, pp. 3382-3395.
McPake et al. (2012) "Selective Continuous Flow Processes Using Fluorine Gas" Org Process Res Dev, vol. 16, No. 5, pp. 844-851.

Métro et al. (2010) "Rearrangement of β-amino alcohols via aziridiniums: a review" Chem Soc Rev, vol. 39, 89-102.
Muller et al. (2007) "Flourine in Pharmaceuticals: Looking Beyond Intuition" Science, vol. 317, No. 5846, pp. 1881-1886.
O'Hagan (2008) "Understanding organofluorine chemistry. An introduction to the C—F bond" Chem Soc Rev, vol. 37, pp. 308-319.
Okoromoba et al. (2014) "Designer HF-Based Fluorination Reagent: Highly Regioselective Synthesis of Fluoroalkenes and gem-Difluoromethylene Compounds from Alkynes" J Am Chem Soc, vol. 136, No. 41, pp. 14381-14384.
Okoromoba et al. (2015) "Preparation of Fluorinated Tetrahydropyrans and Piperidines using a New Nucleophilic Fluorination Reagent DMPU/HF" Org Lett, vol. 17, No. 16, pp. 3975-3977.
Okoromoba et al. (2016) "Achieving regio- and stereo-control in the fluorination of aziridines under acidic conditions" Chem Commun, vol. 52, No. 91, pp. 13353-13356.
Olah et al. (1979) "Synthetic methods and reactions. 63. Pyridinium poly(hydrogen fluoride) (30% pyridine-70% hydrogen fluoride): a convenient reagent for organic fluorination reactions" J Org Chem, vol. 44, No. 22, pp. 3872-3881.
Olah et al. (1990) "Poly-4-vinylpyridinium Poly(hydrogen fluoride): A Convenient Polymeric Fluorinating Agent1" Synlett, vol. 1990, No. 5 pp. 267-269.
Olah et al. (1993) "Poly-4-vinylpyridinium Poly(Hydrogen Fluoride): A Solid Hydrogen Fluoride Equivalent Reagent" Synthesis, vol. 1993, pp. 693-699.
Olah et al. (2007) "Chapter 4 Onium-Poly(Hydrogen Fluorides): Convenient Ionic Liquids for Fluorination and Acid Catalysis" pp. 36-57, in Ionic Liquids in Organic Synthesis, Ed. Sanjay V. Malhotra, ACS Symposium Series vol. 950, American Chemical Society, Washington, DC.
Shimizu et al. (2005) "Modern Synthetic Methods for Fluorine-Substituted Target Molecules" Angew Chem Int Ed, vol. 44, No. 2, pp. 214-231.
Uneyama (2006) Organofluorine chemistry, Blackwell Pub., Oxford; Ames, Iowa. (353 pages).
Van Oosten et al. (2011) "Regioselective ring opening of 2-methylaziridine derivatives with 18F- and 19F-fluoride" Tetrahedron Lett, vol. 52, No. 32, pp. 4114-4116.
Wade (1980) "Preparation of fluoro amines by the reaction of aziridines with hydrogen fluoride in pyridine solution" J Org Chem, vol. 45, No. 26, 5328-5333.
Yadav et al. (2010) "HBF4-OEt2 as a versatile reagent for the Hosomi-Sakurai allylation and Prins cyclization: one-pot synthesis of symmetrical 4-fluorotetrahydropyrans" Tetrahedron Lett, vol. 51, No. 26, pp. 2872-2874.
Zhang et al. (2012) "Synthesis of β-Fluoro Amides Using Partially Hydrated Nickel Difluoride as Fluorine Source" Synlett, vol. 23, No. 16, 2413-2415.
Zhu et al. (2018) "Modern Approaches for Asymmetric Construction of Carbon-Fluorine Quaternary Stereogenic Centers: Synthetic Challenges and Pharmaceutical Needs" Chem Rev, No. 118, pp. 3887-3964.
Zupan et al. (1982) "Synthesis and Properties of Cross-Linked 4-Vinylpyridine-Styrene-Halogen Complexes" J Macromol Sci Chem A, vol. 17, No. 5, pp. 759-769.

* cited by examiner

Scheme 1

Scheme 2

A

Scheme 3

Example Flow Reaction

CATALYSTS, METHODS OF MAKING, AND METHODS OF HYDROFLUORINATION

CROSS-REFERENCE TO RELATED APPLICATIONS

This application is a National Stage Entry of International Application No. PCT/US2019/042770 filed Jul. 22, 2019, entitled "CATALYSTS, METHODS OF MAKING, AND METHODS OF HYDROFLUORINATION" which is herein incorporated by reference in its entirety, and which claims (a) the benefit of U.S. Provisional Application No. 62/702,173 filed Jul. 23, 2018, entitled "METHODS OF HYDROFLUORINATION", which is herein incorporated by reference in its entirety, and (b) the benefit of U.S. Provisional Application No. 62/775,718 filed Dec. 5, 2018, entitled "METHODS OF HYDROFLUORINATION", which is herein incorporated by reference in its entirety.

GOVERNMENT RIGHTS

This invention was made with government support under 1R01GM121660 awarded by the National Institutes of Health. The government has certain rights in the invention.

BACKGROUND

The growing applications of fluorine in pharmaceuticals, agrochemicals, and materials has stimulated interest in fluorination methodologies. Because alkenes can sometimes be important functionalities, finding a broadly applicable alkene hydrofluorination protocol, for example, can help in the preparation of fluorinated compounds. Several hydrofluorination protocols have been developed for alkenes and for other molecules, but they have deficiencies, such as, one or more of: limited to certain alkenes, harsh reaction conditions, use of environmentally undesirable atoms or compounds, required reductants, required expensive electrophilic fluorination reagents, required metal catalysts, use of strong reductants, or use of strong oxidants.

Certain embodiments of the invention address one or more of the deficiencies described above. Some embodiments of the invention include inventive catalysts (e.g., catalysts of Formula (I)). Other embodiments include compositions comprising the inventive catalysts. Some embodiments include methods of using the inventive catalysts (e.g., in hydrofluorination of an organic compound). Further embodiments include methods for making the inventive catalysts. Additional embodiments of the invention are also discussed herein.

SUMMARY

Some embodiments of the present invention include a catalyst selected from Formula (I) resin-anion-xHF (I), where resin is an anion exchange resin, the anion is $HSO_4^-$, $BzO^-$, $AcO^-$, $H_2PO_4^-$, $HPO_4^{2-}$, $PO_4^{3-}$, $MeSO_3^-$, $NO_3^-$, $ReO_4^-$, $CF_3SO_3^-$, $ClO_4^-$, or $CF_3(CF_2)_3SO_3^-$, and x is 1, 2, 3, 4, 5, 6, 7, 8, 9, 10, 11, 12, 13, 14, 15, 16, 17, 18, 19, 20, 21, 22, 23, 24, or 25. In other embodiments, the resin comprises a secondary ammonium group, a tertiary ammonium group, or a quaternary ammonium group. In yet other embodiments, x is 5, 6, 7, 8, 9, 10, 11, 12, 13, 14, 15, 16, 17, 18, 19, or 20. In still other embodiments, x is 5, 10, or 15. In certain embodiments, the anion is $HSO_4^-$, $BzO^-$, $AcO^-$, $H_2PO_4^-$, $HPO_4^{2-}$, or $PO_4^{3-}$. In some embodiments, the anion is $HSO_4^-$. In certain embodiments, (1) the catalyst is resin-$HSO_4^-$-5HF, resin-$HSO_4^-$-10HF, or resin-$HSO_4^-$-15HF, (2) the resin comprises a quaternary ammonium group or trimethylammonium, or (3) both.

Some embodiments of the present invention include a composition comprising any catalyst disclosed herein, and a solvent. In certain embodiments, the solvent is DCM (dichloromethane), DCE (1,2 dichloroethane), dioxane, $Et_2O$ (diethylether), $CH_3CN$, EtOAc (ethyl acetate), DMSO (dimethyl sulfoxide), DMF (dimethyl formamide), or toluene. In other embodiments, the solvent is DCM, DCE, or toluene.

Some embodiments of the present invention include methods for hydrofluorination of a reactant organic compound, the method comprising contacting a composition comprising the reactant organic compound with a composition comprising a catalyst of Formula (I). In certain embodiments, the reactant organic compound is (1) an organic compound comprising one or more alkenes or (2) an organic compound comprising an aziridine. In other embodiments, the composition comprising the reactant organic compound optionally comprises a solvent, the composition comprising the catalyst of Formula (I) optionally comprises a solvent, or both. In certain embodiments, the solvent optionally in each composition can be the same or different. In other embodiments, the composition comprising the reactant organic compound comprises a solvent, the composition comprising a catalyst of Formula (I) comprises a solvent, or both; and the solvent is the same in each composition. In yet other embodiments, the reactant organic compound comprises one or more alkenes and the composition comprising the reactant organic compound further comprises a reactant aldehyde. In still other embodiments, the method comprises (a) providing a composition comprising the solvent and the organic compound comprising one or more alkenes; and (b) contacting the composition of (a) with a composition comprising the catalyst of Formula (I), where the product molecule comprises one F on one of the carbons where an alkene was in the organic compound comprising one or more alkenes. In some embodiments, the composition comprising the reactant organic compound further comprises a reactant aldehyde and the product molecule further comprises a cyclization with the reactant aldehyde. In certain embodiments, the method comprises (a) providing a composition comprising the solvent and the organic compound comprising an aziridine; and (b) contacting the composition of (a) with a composition comprising the catalyst of Formula (I), where the product molecule comprises an opened aziridine ring and an F added to one of the two aziridine ring carbons. In still other embodiments, the contacting in step (b) comprises (i) mixing the composition of (a) with the composition comprising the catalyst of Formula (I) or (ii) moving the composition of (a) through a column with the composition comprising a catalyst of Formula (I). In some embodiments, the composition comprising the catalyst further comprises a solvent which may be the same or different as the solvent in step (a). In other embodiments, the solvent in step (a), step (b) or both is DCE. In yet other embodiments, the catalyst is resin-anion-xHF and x is 5, 10, or 15. In still other embodiments, (1) the catalyst is resin-$HSO_4^-$-5HF, resin-$HSO_4^-$-10HF, or resin-$HSO_4^-$-15HF, (2) the resin comprises a quaternary ammonium group or trimethylammonium, or (3) both. In certain embodiments, the amount of the reactant organic molecule is at least about 0.01 mmol. In some embodiments, the contacting occurs for at least about 0.01 hours. In other embodiments, the contacting occurs for from about 5 hours to about 100 hours. In still other embodiments, the temperature during the contacting is at least about 15° C. In yet other embodiments, the molecular weight of the reactant organic compound, the reactant aldehyde, or both is no more than about 3,000 daltons.

Some embodiments of the present invention include a method for preparing any catalyst disclosed herein comprising (a) optionally contacting the resin with the anion or a salt of anion to produce resin-anion and (b) contacting HF with resin-anion. In other embodiments, the contacting in step (b) is at a temperature of no more than about 20° C. In certain embodiments, the mole ratio of HF to anion (in the resin-anion) is at least about 5.

Other embodiments of the invention are also discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
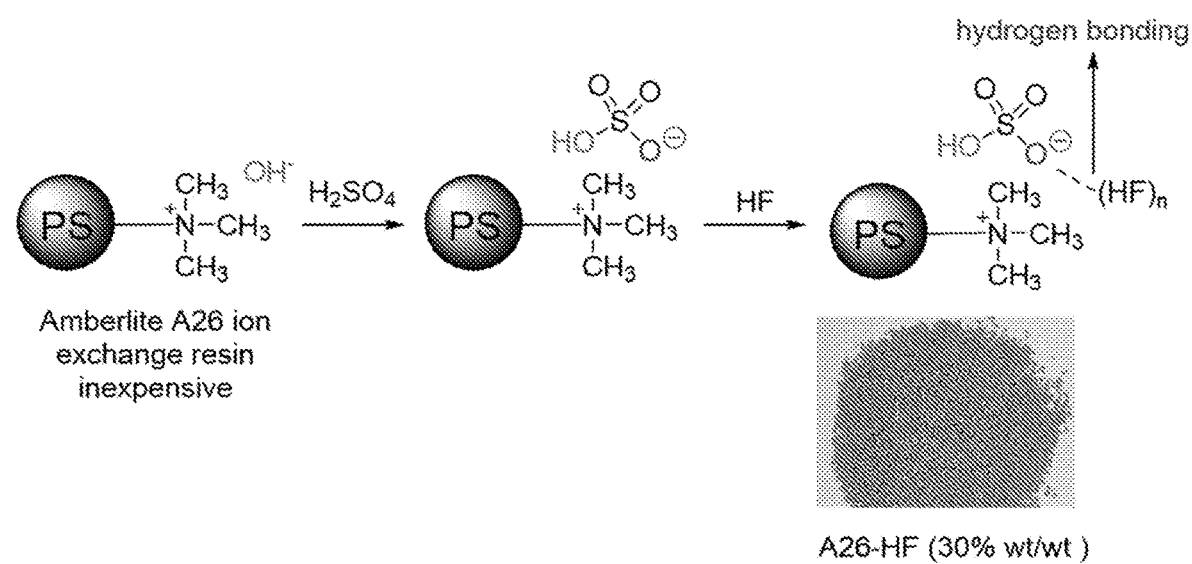
FIG. 1: Scheme 1. Preparation of polymer supported HF reagent.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive catalysts (e.g., catalysts of Formula (I)). Other embodiments include compositions comprising the inventive catalysts. Some embodiments include methods of using the inventive catalysts (e.g., in hydrofluorination of an organic compound). Further embodiments include methods for making the inventive catalysts. Additional embodiments of the invention are also discussed herein.

Some embodiments of the invention include catalysts (e.g., hydrofluorination catalysts) of Formula (I):

resin-anion-xHF    (I).

In some embodiments, the resin can be any suitable resin, such as an anion exchange resin. In certain embodiments, the resin comprises a secondary ammonium group, a tertiary ammonium group, or quaternary ammonium group (e.g., trimethylammonium). In other embodiments, the resin can be Amberlyst A21, Amberlyst A26, Amberlite IRN78, Amberlite IRA743, Amberlite IRA-67 free base, Amberlite IRA-96 free base, Lewatit VP OC 1065, Lewatit MP-62 free base, diaion WA30 free base, diaion WA21J free base, Dowex 66 free base, or TOYOPEARL GigaCap Q-650M/S Bulk Media; these resins can be purchased at Sigma Aldrich (also known as Millipore Sigma and owned by Merck KGaA), St. Louis, Mo. In yet other embodiments, the resin can be Amberlyst A21, Amberlyst A26, or Amberlite IRN78. In still other embodiments, the resin can be Amberlite A26.

In some embodiments, the anion can be $HSO_4^-$, $BzO^-$, $AcO^-$, $H_2PO_4^-$, $HPO_4^{2-}$, $PO_4^{3-}$, $MeSO_3^-$, $NO_3^-$, $ReO_4^-$, $CF_3SO_3^-$, $ClO_4^-$, or $CF_3(CF_2)_3SO_3^-$. In certain embodiments, the anion can be $HSO_4^-$, $BzO^-$, $AcO^-$, $H_2PO_4^-$, $HPO_4^{2-}$, or $PO_4^{3-}$. In yet other embodiments, the anion can be $HSO_4^-$. In some embodiments, the anion is a hydrogen bond acceptor, such as a strong hydrogen bond acceptor. In other embodiments, x can be 1, 2, 3, 4, 5, 6, 7, 8, 9, 10, 11, 12, 13, 14, 15, 16, 17, 18, 19, 20, 21, 22, 23, 24, or 25. In certain embodiments, x can be 5, 6, 7, 8, 9, 10, 11, 12, 13, 14, 15, 16, 17, 18, 19, or 20. In some embodiments, x can be 9, 10, 11, 12, 13, 14, 15, or 16. In some embodiments, x can be 10, 11, 12, 13, 14, or 15. In some embodiments, x can be 5, 10, or 15. In other embodiments, x can be 15.

In some embodiments, the anion has a hydrogen bond basicity (β) of about 7, about 8, about 9, about 10, about 11, about 12, about 13, about 14, about 15, or about 16. In other embodiments, the anion has a hydrogen bond basicity (β) of about 10, about 11, about 12, or about 13. In yet other embodiments, the anion has a pKa of about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5. In some embodiments, the anion has a pKa of about 1.4, about 1.5, about 1.6, about 1.7, about 1.8, about 1.9, about 2.0, about 2.1, about 2.2, or about 2.3.

In some embodiments, (1) the catalyst is resin-$HSO_4^-$-5HF, resin-$HSO_4^-$-10HF, or resin-$HSO_4^-$-15HF, (2) the resin comprises a quaternary ammonium group or trimethylammonium, or (3) both. In other embodiments, (1) the catalyst is resin-$HSO_4^-$-5HF, resin-$HSO_4^-$-10HF, or resin-$HSO_4^-$-15HF and (2) the resin comprises a quaternary ammonium group or trimethylammonium.

Some embodiments of the invention include methods for making catalysts of Formula (I) comprising (a) optionally contacting the resin with an anion (e.g., $H_2SO_4$) or a salt of the anion (e.g., a salt of $H_2SO_4$) to produce resin-anion and (b) contacting HF with resin-anion to produce Formula (I). In other embodiments, step (a) is not optional. In certain embodiments, the resin-anion can be dried prior to step (b). In some embodiments, the anion can be $HSO_4^-$, $BzO^-$, $AcO^-$, $H_2PO_4^-$, $HPO_4^{2-}$, $PO_4^{3-}$, $MeSO_3^-$, $NO_3^-$, $ReO_4^-$, $CF_3SO_3^-$, $ClO_4^-$, or $CF_3(CF_2)_3SO_3^-$. In certain embodiments, the anion can be $HSO_4^-$, $BzO^-$, $AcO^-$, $H_2PO_4^-$, $HPO_4^{2-}$, or $PO_4^{3-}$. In some embodiments, the anion can be $HSO_4^-$. In other embodiments, the salt of the anion can comprise a monovalent cation (e.g., $Li^+$, $Na^+$, $K^+$, $Rb^+$, $Cs^+$, or $NH_4^+$), a divalent cation (e.g., $Ba^{2+}$, $Be^{2+}$, $Cd^{2+}$, $Ca^{2+}$, $Co^{2+}$, $Cu^{2+}$, $Fe^{2+}$, $Mg^{2+}$, or $Mn^{2+}$), or a trivalent cation (e.g., $Fe^{3+}$, $Al^{+3}$, $Cr^{+3}$, $As^{3+}$, or $Bi^{3+}$) or a combination thereof with or without one or more hydrogens (i.e., $H^+$). The contacting in step (a) can be any suitable form of contacting including but not limited soaking the resin in a composition comprising the anion or a salt of the anion, with or without sonication. The contacting in step (b) can be any suitable form of contacting including but not limited to contacting the resin-anion with gaseous HF. In other embodiments, resin-anion is added to a Teflon tube and HF gas (e.g., anhydrous HF gas) is added to the Teflon tube (e.g., with stirring or with shaking). In still other embodiments, the Teflon tube (e.g., prior to adding the HF) can be cooled to any suitable temperature including but not limited to about −20° C., about −10° C., about −5° C., about 0° C., about 5° C., or about 10° C. In yet other embodiments, the Teflon tube during the addition and/or after the addition can be at any suitable temperature (e.g., maintained at a temperature) including but not limited to about −20° C., about −10° C., about −5° C., about 0° C., about 5° C., about 10° C., about 15° C., about 20° C., about 25° C., at least about −20° C., at least about −10° C., at least about 0° C., no more than about 20° C., no more than about 10° C., no more than about 5° C., or no more than about 0° C. In certain embodiments, the mole ratio of added HF to added anion (i.e., the anion in the resin-anion) can be any suitable mole ratio including but not limited to about 0.1, about 0.5, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, at least about 0.1, at least about 1, at least about 5, at least about 10, at least about 15, at least about 20, no more than about 20, or no more than about 25.

In some embodiments, Formula (I) can be stable at room temperature (e.g., about 23° C., or from about 20° C. to about 25° C.) or can be stable at about 4° C. In other embodiments, there is no loss, less than about 0.1% loss, less than about 0.5% loss, or less than about 1.0% loss of HF in a closed container of Formula (I) at room temperature over less than about 0.5 months, less than about 1 month, less than about 2 months, less than about 3 months, less than about 4 months, or less than about 5 months. In other embodiments, there is less than about 0.1% loss, less than about 1.0% loss, less than about 2.0% loss, less than about 3.0% loss, or less than about 4.0% loss of HF in an open container of Formula (I) at room temperature over less than about 10 hours, less than about 20 hours, less than about 30 hours, less than about 40 hours, less than about 50 hours, or less than about 60 hours.

Some embodiments of the invention include compositions comprising catalysts (e.g., hydrofluorination catalysts) of Formulas (I). In certain embodiments, the compositions comprise catalysts of Formula (I) and a solvent. In other embodiments, the solvent is any suitable solvent (e.g., for performing hydrofluorination) including but not limited to DCM (dichloromethane), DCE (1,2 dichloroethane), dioxane, Et$_2$O (diethylether), CH$_3$CN, EtOAc (ethyl acetate), DMSO (dimethyl sulfoxide), DMF (dimethyl formamide), or toluene. In still other embodiments, the solvent is DCM, DCE, or toluene. In yet other embodiments, the solvent is a weak hydrogen bond acceptor. In some embodiments, the composition further comprises an organic compound comprising one or more alkenes or an organic compound comprising an aziridine.

Some embodiments of the present invention include methods for hydrofluorination of a reactant organic compound. In certain embodiments, the reactant organic compound comprises one or more alkenes and the hydrofluorination product can be an altered reactant organic compound which as a result of hydrofluorination has one or more additional fluorines at carbons which previously were part of the one or more alkenes in the reactant organic compound. In other embodiments, the reactant organic compound comprises one or more alkenes which is a reactant in a Fluoro-Prins reaction. In other embodiments, the reactant organic compound comprises an aziridine and the hydrofluorination opens the aziridine ring and adds an F to one of the two aziridine ring carbons. In yet other embodiments, the reactant organic compound can be (a) an organic compound comprising one or more alkenes or (b) an organic compound comprising an aziridine.

In other embodiments of the methods for hydrofluorination, the reactant organic compound comprising one or more alkenes can comprise any suitable alkene including but not limited to alkenes that are:

(a) monosubstituted alkenes (e.g.,

to provide

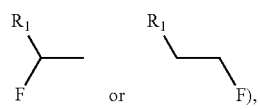

(b) disubstituted alkenes (e.g.,

to provide

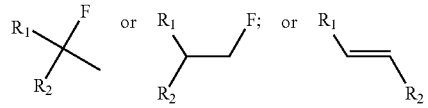

to provide

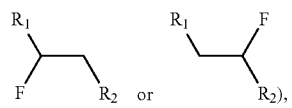

or (c) trisubstituted alkenes (e.g.,

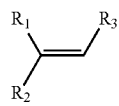

to provide

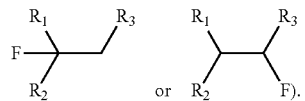

In some embodiments, at least one alkene in the reactant organic compound comprising one or more alkenes is not monosubstituted. In some embodiments, $R_1$, $R_2$, and $R_3$ can comprise or be any suitable moiety, such as but not limited to those provided in the Examples. In other embodiments, one or more of $R_1$, $R_2$, or $R_3$ can comprise one or more of any moiety such as but not limited to one or more of ester, sulfonate, amide, ether, nitro, nitrile, aldehyde, amine, heterocycle, quinoline, furan, thiophene, pyridine, indazole, benzotriazole, pyrrole, thiazole, alcohol, primary alcohol, secondary alcohol, tertiary alcohol, ketones, α, β unsaturated ketone, carboxylic acid, halogen, aryl, benzyl, phenyl, heteroaryl, alkyl, alkenyl, alkynyl, alkoxy, —CN, sulfo, morpholinyl, —CONH$_2$, —CON(CH$_3$)$_2$, $C_1$-$C_3$ perfluoronated alkyl, —CF$_3$, —OCF$_3$, or cyclic alkyl (e.g., cyclopropyl). In some embodiments, the reactant organic compound comprising one or more alkenes may or may not comprise an aziridine. In certain embodiments, the alkene comprises basic moieties. In some embodiments, one or more of $R_1$, $R_2$, or $R_3$ can be a short alkyl (e.g., $C_1$, $C_2$, $C_3$, $C_4$, $C_5$, $C_6$, or $C_7$ alkyl). In certain embodiments, hydrofluorination can occur at the alkene carbon that has more substitutions (e.g., as per Markovnikov's rule). In other embodiments, if there is more than one alkene, the hydrofluorination can occur at the alkene that is more electron rich (e.g., having a higher HOMO orbital energy and/or density). In yet other embodiments, hydrofluorination does not occur at monosubstituted alkenes. In still other embodiments, the hydrofluorination does not open a cyclopentyl moiety.

In some embodiments of the methods for hydrofluorination, the organic compound comprising one or more alkenes can be a reactant in a Fluoro-Prins reaction where the organic compound comprising one or more alkenes reacts with a reactant aldehyde (e.g.,

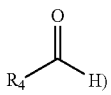

to produce a cyclic structure with one or more oxygens in the ring. In certain embodiments, at least one of the alkenes in the organic compound comprising one or more alkenes is a monosubstituted alkene, a disubstituted alkene, or a trisubstituted alkene. In other embodiments, at least one of the alkenes in the organic compound comprising one or more alkenes is a monosubstituted alkene or a disubstituted alkene. In other embodiments, $R_4$ can comprise one or more of any moiety such as but not limited those shown or inferred from the Examples. In yet other embodiments, $R_4$ can comprise one or more of any moiety such as but not limited to one or more of ester, sulfonate, amide, ether, nitro, nitrile, aldehyde, amine, heterocycle, quinoline, furan, thiophene, pyridine, indazole, benzotriazole, pyrrole, thiazole, alcohol, primary alcohol, secondary alcohol, tertiary alcohol, ketones, α, β unsaturated ketone, carboxylic acid, halogen, aryl, benzyl, phenyl, heteroaryl, alkyl, alkenyl, alkynyl, alkoxy, —CN, sulfo, morpholinyl, —CONH$_2$, —CON(CH$_3$)$_2$, $C_1$-$C_3$ perfluoronated alkyl, —CF$_3$, —OCF$_3$, or cyclic alkyl (e.g., cyclopropyl). In other embodiments, the reactant aldehyde comprises a cyclic structure (e.g., substituted or unsubstituted aryl (e.g., phenyl), substituted or unsubstituted heteroaryl, substituted or unsubstituted cycloalkyl, or substituted or unsubstituted heterocyclyl). In certain embodiments, the reactant organic compound comprising one or more alkenes has at least one alkene in a $C_4$ linear portion of the organic compound. In other embodiments, the reactant organic compound comprising one or more alkenes is

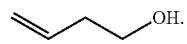

In some embodiments, cyclization with the reactant aldehyde can occur. In certain embodiments, the cyclization proceeds through a chair transition states with a syn addition of the nucleophile across an alkene.

In some embodiments of the methods for hydrofluorination, the reactant organic compound comprises an aziridine (e.g.,

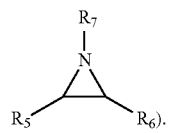

In some embodiments, $R_5$, $R_6$, and $R_7$ can comprise or be any suitable moiety, such as but not limited to those provided in the Examples. In other embodiments, one or more of $R_5$, $R_6$, or $R_7$ can comprise one or more of any moiety such as but not limited to one or more of ester, sulfonate, amide, ether, nitro, nitrile, aldehyde, amine, heterocycle, quinoline, furan, thiophene, pyridine, indazole, benzotriazole, pyrrole, thiazole, alcohol, primary alcohol, secondary alcohol, tertiary alcohol, ketones, α, β unsaturated ketone, carboxylic acid, halogen, aryl, benzyl, phenyl, heteroaryl, alkyl, alkenyl, alkynyl, alkoxy, —CN, sulfo, morpholinyl, —CONH$_2$, —CON(CH$_3$)$_2$, $C_1$-$C_3$ perfluoronated alkyl, —CF$_3$, —OCF$_3$, or cyclic alkyl (e.g., cyclopropyl). In certain embodiments, the $R_5$, $R_6$, or $R_7$ comprise basic moieties. In some embodiments, one or more of $R_5$, $R_6$, or $R_7$ can be a short alkyl (e.g., $C_1$, $C_2$, $C_3$, $C_4$, $C_5$, $C_6$, or $C_7$ alkyl). In some embodiments, one or more of $R_5$, $R_6$, or $R_7$ comprises an N-protecting group such as but not limited to tosyl, benzoyl, or carboxybenzyl. In some embodiments, the reactant organic compound comprising an aziridine (e.g., none $R_5$, $R_6$, and $R_7$) that does not comprise an alkene. In some embodiments, the reactant organic compound comprising an aziridine (e.g., one or more of $R_5$, $R_6$, or $R_7$) that does comprise an alkene. In other embodiments when one or more of $R_5$, $R_6$, or $R_7$ is an N-protecting group, at least one N-protecting group is not chemically changed by the hydrofluorination reaction.

In some embodiments, the reactant organic compound (e.g., comprising one or more alkenes or comprising an aziridine) or the reactant aldehyde can have any suitable molecular weight including but not limited to about 28 daltons, about 100 daltons, about 200 daltons, about 300 daltons, about 400 daltons, about 500 daltons, about 600 daltons, about 700 daltons, about 800 daltons, about 900 daltons, about 1,000 daltons, about 5,000 daltons, about 10,000 daltons, about 20,000 daltons, about 30,000 daltons, about 40,000 daltons, about 50,000 daltons, about 75,000 daltons, about 100,000 daltons, about 250,000 daltons, about 1,000,000 daltons, at least about 28 daltons, at least about 100 daltons, at least about 200 daltons, no more than about 100 daltons, no more than about 1,000 daltons, no more than about 5,000 daltons, no more than about 10,000 daltons, no more than about 50,000 daltons, no more than about 100,000 daltons, no more than about 500,000 daltons, or no more than about 1,000,000 daltons.

In some embodiments, methods for hydrofluorination can comprise contacting a composition comprising a reactant organic compound (e.g., comprising one or more alkenes or comprising an aziridine) with a catalyst of Formula (I) to provide a product molecule. In certain embodiments, the contacting is in the presence of a solvent (e.g., with the organic compound, with the catalyst, or both). In other embodiments, methods for hydrofluorination can comprise (a) providing a composition comprising a solvent and the reactant organic compound (e.g., comprising one or more alkenes or comprising an aziridine) (e.g., adding the solvent to the organic compound or adding the organic compound to the solvent), and then (b) contacting the composition of (a) with a composition comprising a catalyst of Formula (I) to provide a product molecule. In other embodiments, the composition comprising a catalyst of Formula (I) further comprises a solvent, which can be the same or different from the solvent in step (a). In some embodiments, the contacting is step (b) can be any suitable method such as but not limited to (i) mixing the composition of (a) with a catalyst of Formula (I) or (ii) moving the composition of (a) through a column comprising a catalyst of Formula (I) with or without the solvent (the solvent of step (b) can be the same or different as the solvent of the composition of (a)). In certain embodiments, when a column is used in step (b), the solvent can be added (e.g., flashed) to the column prior to step (b). In some embodiments, the column can be any suitable size including but not limited to 6 mm×250 mm.

In certain embodiments of the methods for hydrofluorination, Formula (I) can be any Formula (I) disclosed herein. In some embodiments, the resin can be any suitable resin, such as an anion exchange resin. In certain embodiments, the resin comprises a secondary ammonium group, a tertiary ammonium group, or quaternary ammonium group (e.g., trimethylammonium). In other embodiments, the resin can be Amberlyst A21, Amberlyst A26, Amberlite IRN78, Amberlite IRA743, Amberlite IRA-67 free base, Amberlite IRA-96 free base, Lewatit VP OC 1065, Lewatit MP-62 free base, diaion WA30 free base, diaion WA21J free base, Dowex 66 free base, or TOYOPEARL GigaCap Q-650M/S Bulk Media. In yet other embodiments, the resin can be Amberlyst A21, Amberlyst A26, or Amberlite IRN78. In still other embodiments, the resin can be Amberlite A26. In certain embodiments, the anion can be $HSO_4^-$, $BzO^-$, $AcO^-$, $H_2PO_4^-$, $HPO_4^{2-}$, $PO_4^{3-}$, $MeSO_3^-$, $NO_3^-$, $ReO_4^-$, $CF_3SO_3^-$, $ClO_4^-$, or $CF_3(CF_2)_3SO_3^-$. In certain embodiments, the anion can be $HSO_4^-$, $BzO^-$, $AcO^-$, $H_2PO_4^-$, $HPO_4^{2-}$, or $PO_4^{3-}$. In yet other embodiments, the anion can be $HSO_4^-$. In other embodiments, x can be 1, 2, 3, 4, 5, 6, 7, 8, 9, 10, 11, 12, 13, 14, 15, 16, 17, 18, 19, 20, 21, 22, 23, 24, or 25. In certain embodiments, x can be 5, 6, 7, 8, 9, 10, 11, 12, 13, 14, 15, 16, 17, 18, 19, or 20. In some embodiments, x can be 9, 10, 11, 12, 13, 14, 15, or 16. In some embodiments, x can be 10, 11, 12, 13, 14, or 15. In some embodiments, x can be 5, 10, or 15. In other embodiments, x can be 15.

In other embodiments of the methods for hydrofluorination, the solvent is any suitable solvent (e.g., for performing hydrofluorination) including but not limited to DCM (dichloromethane), DCE (1,2 dichloroethane), dioxane, $Et_2O$ (diethylether), $CH_3CN$, EtOAc (ethyl acetate), DMSO (dimethyl sulfoxide), DMF (dimethyl formamide), or toluene. In still other embodiments, the solvent is DCM, DCE, or toluene. In yet other embodiments, the solvent is a weak hydrogen bond acceptor.

In some embodiments, the amount of the reactant organic molecule (e.g., comprising one or more alkenes or comprising an aziridine) (e.g., in (a) or in (b)) or the reactant aldehyde can be any suitable amount including but not limited to about 0.01 mmol, about 0.05 mmol, about 0.1 mmol, about 0.2 mmol, about 0.3 mmol, about 0.4 mmol, about 0.5 mmol, about 1 mmol, about 2 mmol, about 3 mmol, about 4 mmol, about 5 mmol, about 6 mmol, about 7 mmol, about 8 mmol, about 9 mmol, about 10 mmol, about 12 mmol, about 15 mmol, about 20 mmol, about 30 mmol, about 50 mmol, about 70 mmol, at least about 0.01 mmol, at least about 0.1 mmol, at least about 1 mmol, no more than about 1 mmol, no more than about 10 mmol, no more than about 15 mmol, no more than about 30 mmol, or no more than about 70 mmol. In some embodiments, the amount of the reactant organic molecule (e.g., comprising one or more alkenes or comprising an aziridine) (e.g., in (a) or in (b)) or the reactant aldehyde can be any suitable amount including but not limited to about 0.001 M, about 0.01 M, about 0.05 M, about 0.1 M, about 0.2 M, about 0.3 M, about 0.4 M, about 0.5 M, about 0.6 M, about 0.7 M, about 0.8 M, about 0.9 M, about 1.0 M, about 1.5 M, about 2.0 M, about 2.5 M, about 3.0 M, about 4.0 M, about 5.0 M, about 6.0 M, about 7.0 M, about 8.0 M, about 9.0 M, about 10.0 M, at least about 0.001 M, at least about 0.01 M, at least about 0.05 M, at least about 0.1 M, no more than about 10.0 M, no more than about 7.0 M, no more than about 5.0 M, no more than about 3.0 M, or no more than about 1.0 M.

In some embodiments, the catalyst is resin-anion-xHF and x is 5, 10, or 15. In other embodiments, the catalyst is resin-$HSO_4^-$-xHF and x is 5, 10, or 15. In certain embodiments, (1) the catalyst is resin-$HSO_4^-$-5HF, resin-$HSO_4^-$-10HF, or resin-$HSO_4^-$-15HF, (2) the resin comprises a quaternary ammonium group or trimethylammonium, or (3) both. In certain embodiments, (1) the catalyst is resin-$HSO_4^-$-5HF, resin-$HSO_4^-$-10HF, or resin-$HSO_4^-$-15HF and (2) the resin comprises a quaternary ammonium group or trimethylammonium.

In other embodiments, in step (b) the composition of (a) (e.g., prior to contacting) can be at any suitable temperature including but not limited to about room temperature (e.g., about 23° C., or from about 20° C. to about 25° C.), about –10° C., about –5° C., about 0° C., about 10° C., about 15° C., about 20° C., about 23° C., about 25° C., about 30° C., about 35° C., about 40° C., about 50° C., about 55° C., about 60° C., about 70° C., about 80° C., no more than about 60° C., no more than about 50° C., at least about –10° C., at least about 10° C., or at least about 20° C.

In some embodiments, the contacting can occur under any suitable pressure including but not limited to about 0.1 atm, about 0.5 atm, about 1.0 atm, about 1.5 atm, about 2.0 atm, at least about 0.1 atm, at least about 0.5 atm, no more than 1.5 atm, or no more than 2.0 atm. The pressure can be the same or different in each step in the method.

In some embodiments, the composition of (a) is added to a composition comprising a catalyst of Formula (I) in one portion, two portions, three portions, five portions, at least two portions, at least five portions, or no more than five portions. In other embodiments, the composition comprising a catalyst of Formula (I) is added to the composition of (a) in one portion, two portions, three portions, five portions, at least two portions, at least five portions, or no more than five portions. In certain embodiments, the catalyst can be at any suitable temperature (e.g., prior to or when being added to a solution, or prior to or if a solution is being added to it) including but not limited to about room temperature (e.g., about 23° C., or from about 20° C. to about 25° C.), about −10° C., about −5° C., about 0° C., about 10° C., about 15° C., about 20° C., about 23° C., about 25° C., about 30° C., about 35° C., about 40° C., about 50° C., about 55° C., about 60° C., about 70° C., about 80° C., no more than about 60° C., no more than about 50° C., at least about −10° C., at least about 10° C., or at least about 20° C. In other embodiments, the contacting (e.g., in step (b)) occurs by mixing, stirring, shaking, or being in a column, any of which can occur at any suitable temperature including but not limited to about room temperature (e.g., about 23° C., or from about 20° C. to about 25° C.), about −10° C., about −5° C., about 0° C., about 10° C., about 15° C., about 20° C., about 25° C., about 30° C., about 35° C., about 40° C., about 50° C., about 55° C., about 60° C., about 70° C., about 80° C., no more than about 60° C., no more than about 50° C., at least about −10° C., at least about 10° C., at least about 15° C., or at least about 20° C. In certain embodiments, the amount of time of contacting (e.g., in step (b)) can be any suitable time including but not limited to about 0.01 hours (h), about 0.1 h, about 0.2 h, about 0.3 h, about 0.4 h, about 0.5 h, about 0.6 h, about 0.7 h, about 0.8 h, about 0.9 h, about 1.0 h, about 1.5 h, about 2.0 h, about 3.0 h, about 4.0 h, about 5.0 h, about 10 h, about 15 h, about 18 h, about 20 h, about 25 h, about 30 h, about 40 h, about 50 h, about 100 h, at least about 0.01 h, at least about 0.1 h, at least about 0.5 h, no more than about 100 h, no more than about 20 h, no more than about 5.0 h, or no more than about 1 h. In some embodiments, the HF equivalence of the catalyst of Formula (I) to the reactant organic compound (e.g., comprising one or more alkenes or comprising an aziridine) or to the reactant aldehyde can be any suitable value including but not limited to about 0.001, about 0.01, about 0.05, about 0.1, about 0.2, about 0.3, about 0.4, about 0.5, about 0.6, about 0.7, about 0.8, about 0.9, about 1.0, about 1.5, about 2.0, about 2.5, about 3.0, about 4.0, about 5.0, about 10, about 15, about 20, about 30, about 40, about 50, at least about 0.001, at least about 0.01, at least about 0.1, at least about 0.5, at least about 1.0, at least about 5.0, no more than about 1.0, no more than about 5.0, no more than about 30, or no more than about 50. In some instances, the reaction can be monitored using any suitable method including but not limited to using TLC.

In other embodiments, the reaction can be cooled (e.g., to about 0° C.). In still other embodiments, the reaction can be quenched using any suitable method such as but not limited to cooling or adding $CaCO_3$.

In certain embodiments of the methods for hydrofluorination, the product molecule can be optionally or further recovered. Recovery can occur using any suitable method including but not limited to one or more of HPLC (e.g., reverse phase), LC, filtration (e.g., through kieselguhr), precipitation, concentrated, centrifugation, column chromatography (e.g., size exclusion chromatography, ion exchange chromatography, or flash chromatography), use of silica gel, washings (e.g., one or more time with one or more solvents or solvent mixtures), or combinations thereof.

The presently-disclosed subject matter is further illustrated by the following specific but non-limiting examples. The following examples may include compilations of data that are representative of data gathered at various times during the course of development and experimentation related to the present invention.

EXAMPLES

Some methods, figures, and discussion of the experiments in these Examples can be found in LU et al. (2019) "Multifaceted ion exchange resin-supported hydrogen fluoride: a path to flow hydrofluorination" Green Chemistry, Vol. 21, pp. 2224-2228 and related Supporting Information, which is herein incorporated by reference in its entirety.

Section 1. Experimental Details $^1$H NMR and $^{13}$C NMR spectra were recorded at 400 MHz and 100 MHz respectively, using $CDCl_3$ as a solvent. The chemical shifts are reported in δ (ppm) values relative to $CHCl_3$ (δ 7.26 ppm for $^1$H NMR), multiplicities are indicated by s (singlet), d (doublet), t (triplet), q (quartet), p (pentet), h (hextet), m (multiplet) and br (broad). Coupling constants, J, are reported in Hertz.

Solvents like DCM, $Et_2O$, Toluene, DMF were chemically dried using a commercial solvent purification system. Other solvents like DCE, dioxane, EtOAc and DMSO were dried with activated 4 Å molecular sieves overnight. Anhydrous hydrogen fluoride (HF) gas cylinder was purchased from Synquest Laboratories Inc. The three anionic ion exchange resins—Amberlite IRN78 hydroxide form, Amberlyst A21 free base and Amberlyst A26 hydroxide form were from sigma Aldrich.

All other reagents and solvents were employed without further purification. The products were purified using a CombiFlash system. TLC was developed on Merck silica gel 60 F254 aluminum sheets and $KMnO_4$ stain was used for TLC developing. $KMnO_4$ stain was prepared by dissolving $KMnO_4$ (1.5 g), $K_2CO_3$ (10 g), and NaOH (10 wt %, 1.25 mL) in 200 mL water. All NMR solvents were purchased from Cambridge Isotope Laboratories, Inc.

Most of the substrates in the reactions were purchased or synthesized according to the literature. Therefore, we only used $^1$H NMR spectra to confirm the identity of those known compounds.

Section 2. Examples of Preparation of Resin-HF Complex

Properties of the Anionic Resins:

Amberlite IRN78 hydroxide form (capacity: 1.1 meq/mL by wetted bed volume), Amberlyst A21 free base (capacity: 1.3 meq/mL by wetted bed volume), and Amberlyst A26 hydroxide form (capacity: 0.8 meq/mL by wetted bed volume).

Scheme 1 in FIG. 1 shows the preparation of polymer supported HF reagent.

Step 1: Modification of the Resin with $H_2SO_4$ (Taking Amberlyst A26 Hydroxide Form as Example)

Concentrated sulfuric acid (98%, 5.2 mL) diluted with deionized water (150 mL) were prepared and divided into 3 aliquots. Wet A26 resin (40 mL) was soaked in the aliquot of diluted $H_2SO_4$ solution and sonicated for 0.5 hour. The aqueous solution was decanted and the sediment resin was retreated the $H_2SO_4$ aliquots twice. The modified resin with washed with water (50 mL×3), ethanol (50 mL×2) sequentially and then dried on rotavapor to afford modified resin (9.5 g).

To calculate the volume for 3 equivalents of concentrated $H_2SO_4$:

40 mL resin×0.8 meq/mL×3 equiv $H_2SO_4$×0.001 mol/mmol×98 g/mol÷98%÷1.84 g/mL=5.2 mL $H_2SO_4$.

Figure 2:
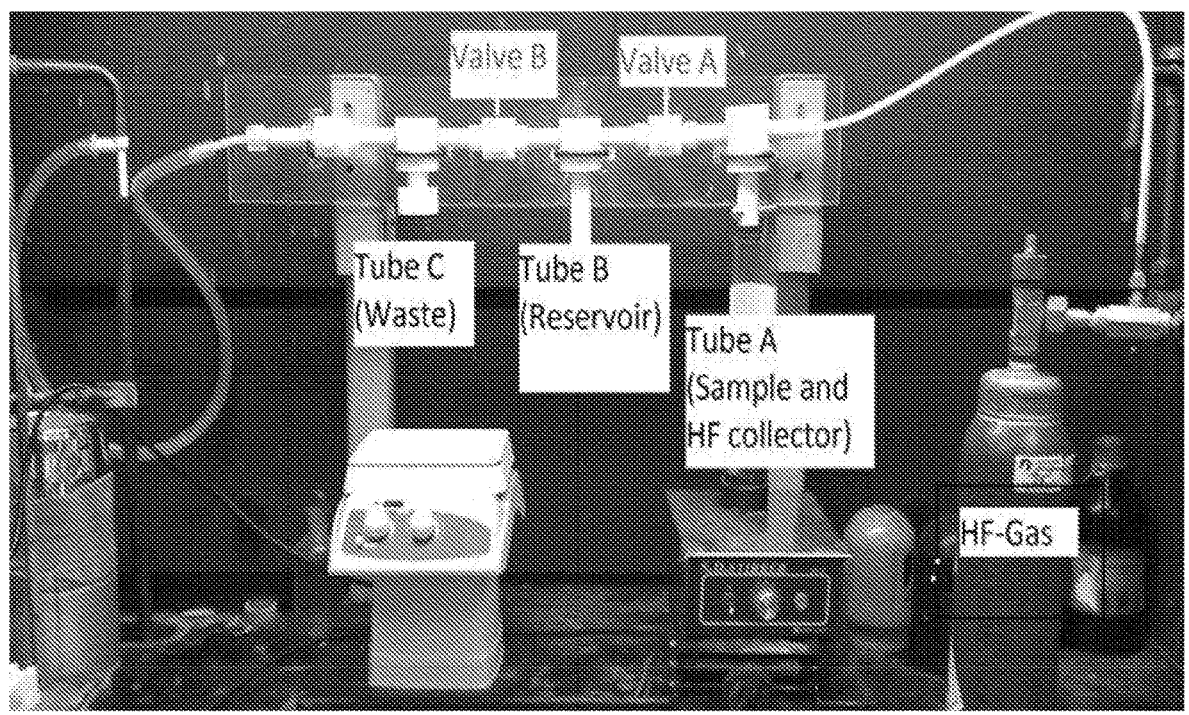
FIG. 2: Scheme 2. Complex modified resin with anhydrous hydrogen fluoride.

Step 2: Complex Modified Resin with Anhydrous Hydrogen Fluoride:

See Scheme 2 shown in FIG. 2. The modified resin (5 g) was added into a long Teflon tube (Tube A) which was cooled to 0° C. Anhydrous HF gas was then condensed into the Teflon tube A under stirring. The obtained complex was poured to a High-density polyethylene (HDPE) bottle (30 mL) with a screw cap. It is bench stable, but for long term storage, it was stored in a refrigerator (4° C.).

Thermostability Test for the Resin HF Complex:

At room temperature, we did not detect noticeable HF loss in a capped polypropylene container over 2 months. To investigate the stability and safety profile of the ion exchange-supported HF reagent, we conducted an HF loss experiment in open air at room temperature in a well-vented fume hood. $HSO_4^-$ A26 resin-HF complex (HF 30% wt/wt) (1.45 g) was introduced into a 8 mL polypropylene vial, the vial was left at room temperature in open air. Similar experiments were performed at 50° C. in open air. See FIGS. 3A and 3B.

Section 3. Example Flow Reaction with Resin-HF Complex.

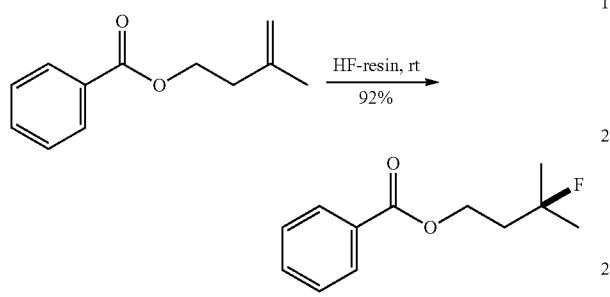

Figure 4:
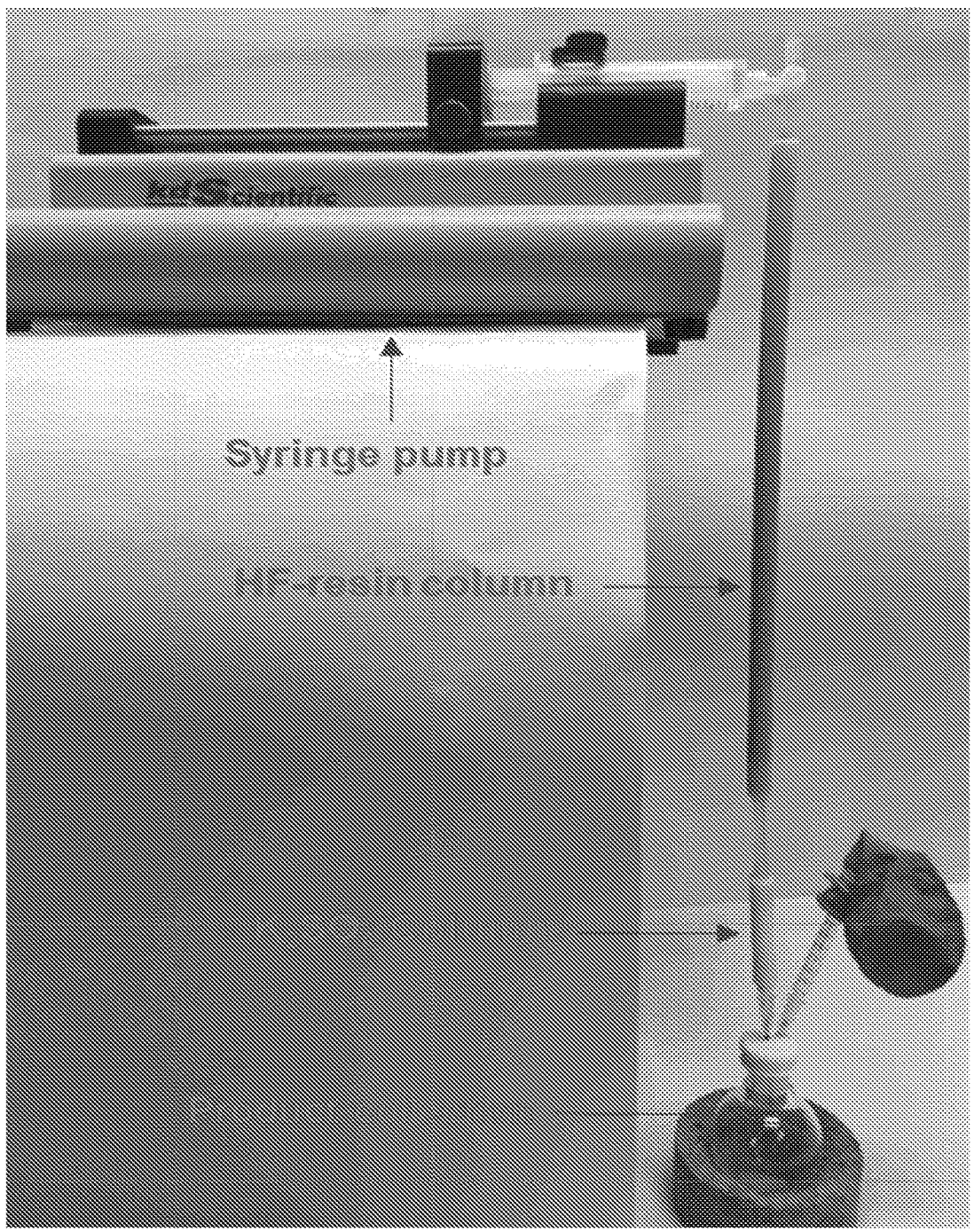
FIG. 4: Scheme 3. Flow reaction with polymer supported HF reagent.

$HSO_4^-$ A26 resin-HF (30%) (4.4 g) was loaded into an empty column (6 mm*250 mm) made by PTFE tube. The starting material (0.57 g) was injected into the column and flashed with dry DCE at 0.5 mL/h flow rate. A 6 mm×50 mm column charged with $K_2SO_4$ was attached to remove excess HF in the eluent. A flask (50 mL) equipped with a balloon buffer was attached to the $K_2SO_4$ column to collect the final product solution (see Scheme 3 in FIG. 4).

Section 4. Example Preparation of Substrates

Synthesized alkene substrates 1 (these substrates were confirmed with $^1H$ and $^{13}C$ NMR spectra).

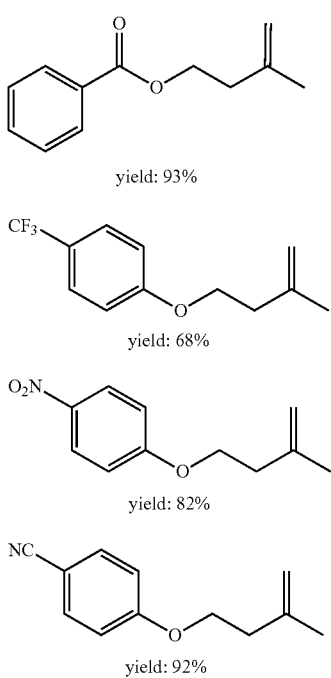

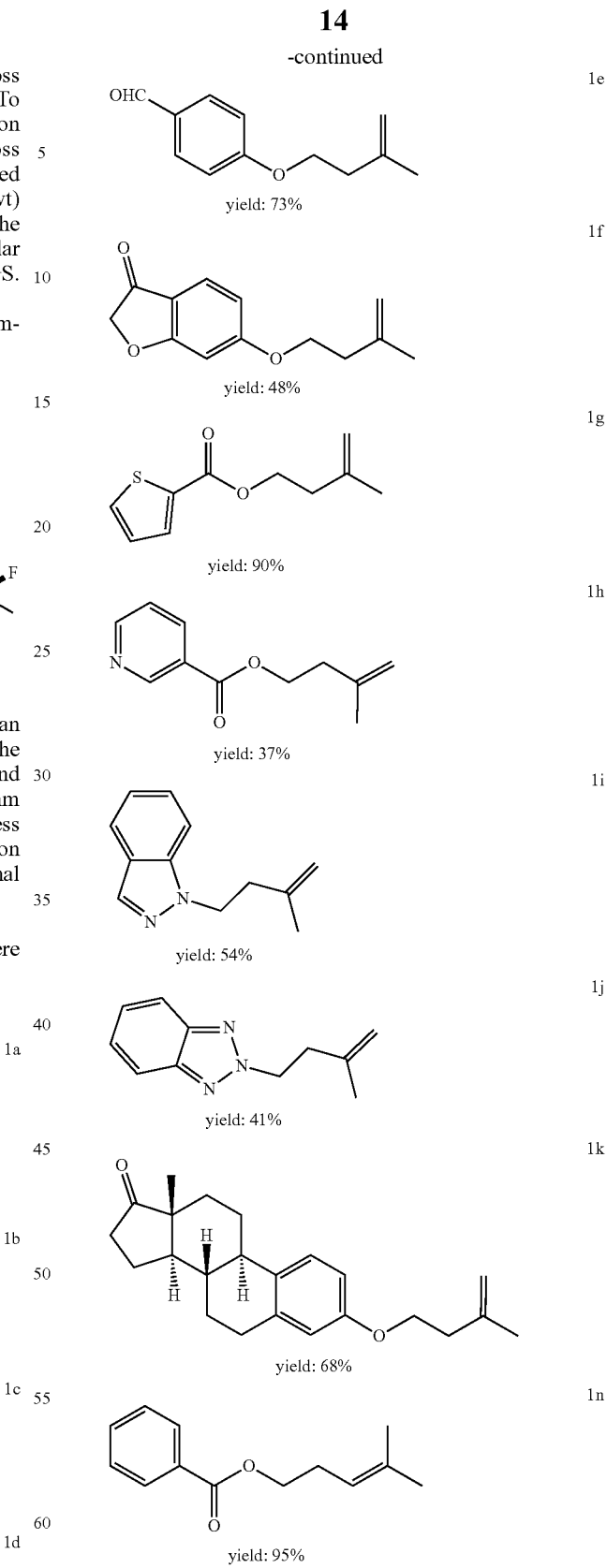

Synthesized aziridine substrates 3 (these substrates were synthesized and confirmed with the literature data by their NMR spectra). For example, see OKOROMOBA et al. 2016 (OKOROMOBA et al. (2016) "Achieving regio- and stereo-control in the fluorination of aziridines under acidic conditions" Chem. Commun., Vol. 52, pp. 13353-13356.).

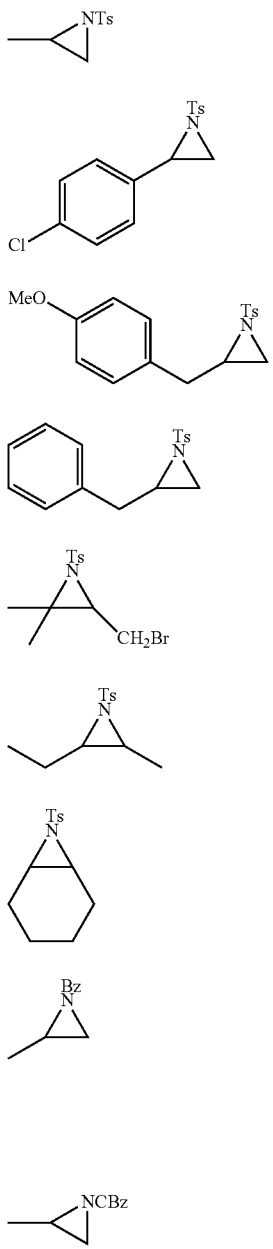

Alkene Substrates from Commercial Sources

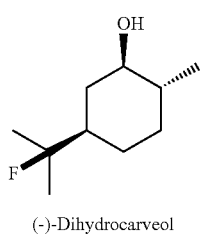

(-)-Dihydrocarveol

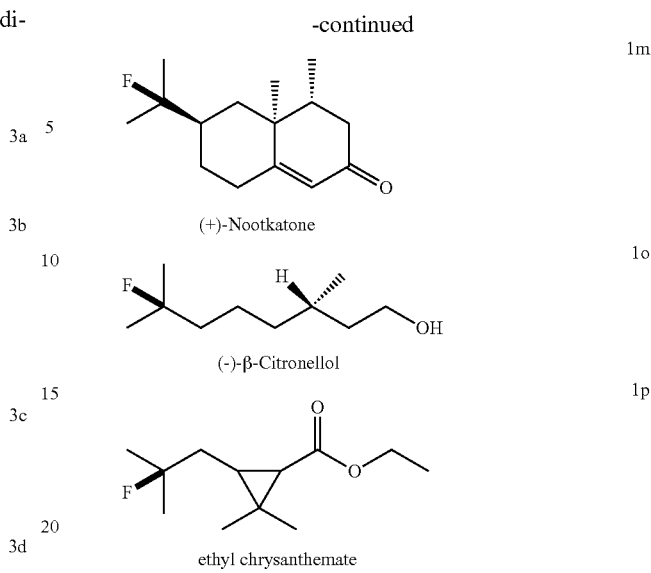

(+)-Nootkatone (-)-β-Citronellol ethyl chrysanthemate

Example Synthetic Procedure for the Synthesis of Esters 1a, 1g, 1n.

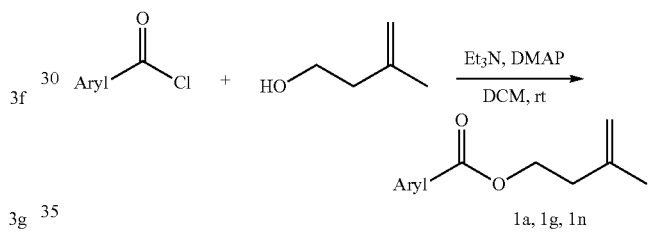

A 20-mL vial fitted with a stirring bar was charged with alcohol (2 mmol), Et₃N (2 equiv) and dry DCM (10 mL). The mixture was cooled down to 0° C. and benzoyl chloride (1.2 equiv) and 5 mg DMAP were then added sequentially. The mixture was stirred overnight and then it was diluted with 50 mL DCM, washed with 1M aqueous HCl (2×20 mL), saturated NaHCO₃ (20 mL) and brine (20 mL), sequentially. The organic layer was then dried with Na₂SO₄ and concentrated. The residue was purified with column chromatography to afford the desired esters 1a (yield: 93%), 1g (yield: 90%), 1n (yield: 95%).

Example Synthetic Procedure for the Synthesis of Ethers 1b, 1c, 1d, 1e, 1f, 1k.

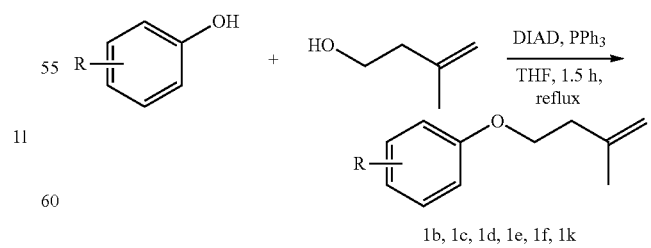

A solution of phenol (3 mmol), 3-methyl-3-buten-1-ol (3.6 mmol), triphenylphosphine (3.6 mmol), diisopropyl azodicarboxylate (3.6 mmol) in THF (27 mL) was heated for 1.5 hours at reflux. After concentrated in vacuo, the residue was purified by flash column chromatography to give the desired ethers 1b (yield: 68%), 1c (yield: 82%), 1d (yield: 92%), 1e (yield: 73%), 1f (yield: 48%), 1k (yield: 68%).

Example Synthetic Procedure for the Synthesis of 1i, 1j.

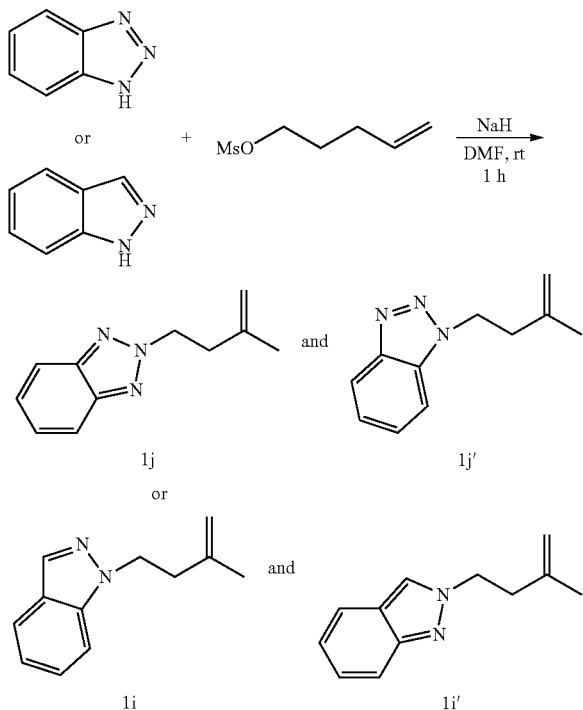

A 50-mL flask fitted with a stirring bar was charged with a solution of starting material (2 mmol) in DMF (10 mL). The mixture was cooled down to 0° C. and NaH (1.5 equiv) was then added. The mesylate was also added and the mixture was stirred at rt for 1 h. The reaction was quenched by NH$_4$Cl (1 M) and diluted with CH$_2$Cl$_2$ (50 mL). After being washed with 5% LiCl aqueous solution (2×20 mL), the aqueous layer was extracted with CH$_2$Cl$_2$ (20 mL). The combined organic extracts were washed with water (20 mL), dried and concentrated in vacuo. The resulting residues was purified by silica gel flash chromatography to afford 1i (yield: 54%), 1i' (yield: 30%), 1j (yield: 41%), 1j' (yield: 40%).

Example Synthetic Procedure for the Preparation of Ester 1h.

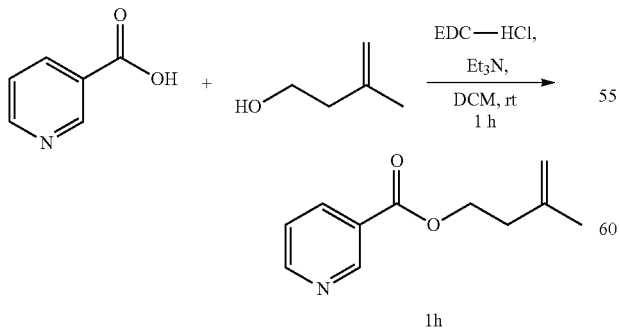

A 50-mL flask fitted with a stirring bar was charged with a solution of alcohol (2 mmol), EDCI (1.2 equiv), triethylamine (1.5 equiv), and DMAP (0.1 equiv) in dichloromethane (10 mL). Nicotinic acid (1 equiv) was then added at 0° C. and the reaction mixture was stirred overnight at room temperature. After the reaction was complete, the resulting mixture was diluted with DCM (50 mL), washed by 1 N HCl (2×20 mL), 1 N aqueous NaHCO$_3$ (2×20 mL), and brine (1×20 mL). The organic layer was dried (Na$_2$SO$_4$) and evaporated in vacuo. The resulting residue was purified by column chromatography to afford the desired ester 1h (yield: 37%).

Section 5. Example Procedures for Reactions with Resin-HF Complex 5.1 Hydrofluorination of Alkenes.

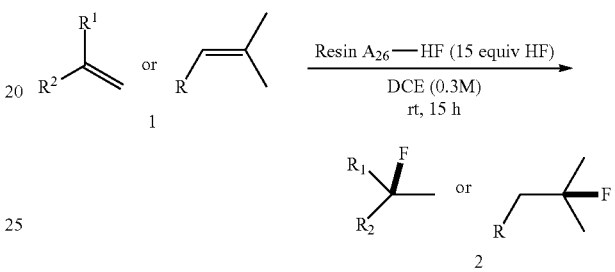

An 8-mL Polytetrafluoroethylene (PTFE) vial fitted with a stirring bar was charged with dry DCE (0.6 mL) and alkene starting material (0.2 mmol). HSO$_4^-$ A26 Resin-HF (200 mg, 15.0 equiv based on HF) was then added in one portion at room temperature. The progress of reaction was monitored by TLC (visualized by KMnO$_4$ stain). The product usually shows a slightly more polar spot than the starting material on TLC($R_f$ difference<0.1 in most cases). The reaction was then filtered, and the resin was washed with ethyl acetate (2 mL×2). The filtrate was concentrated, and the residue was purified with flash chromatography.

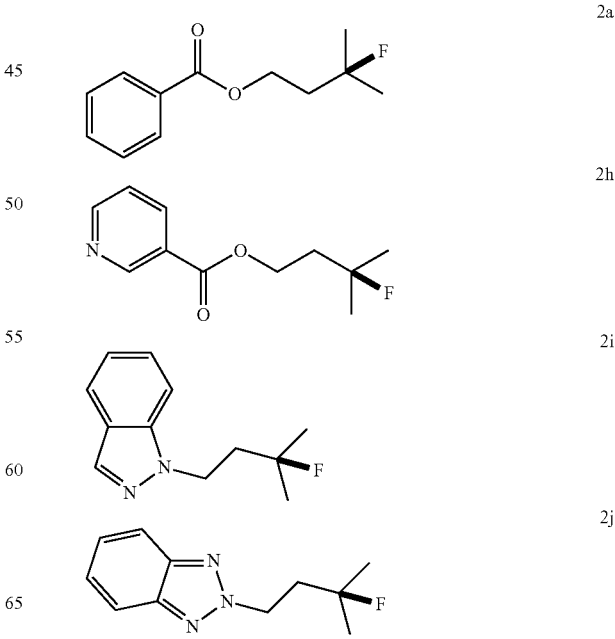

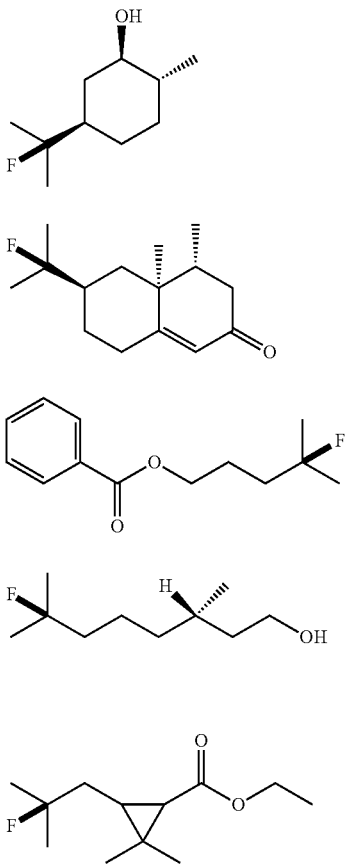

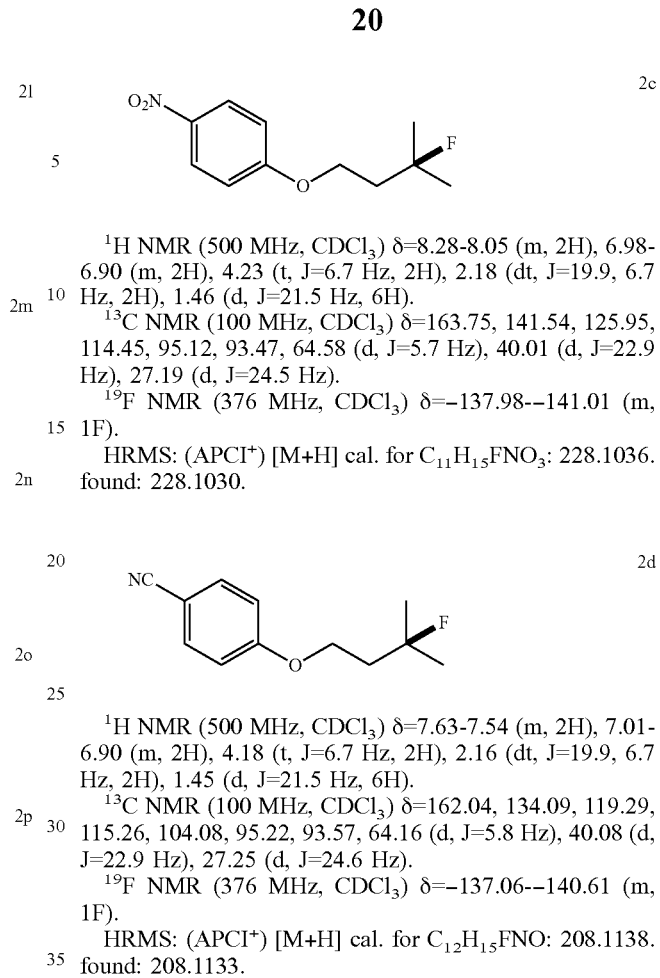

¹H NMR (500 MHz, CDCl₃) δ=8.28-8.05 (m, 2H), 6.98-6.90 (m, 2H), 4.23 (t, J=6.7 Hz, 2H), 2.18 (dt, J=19.9, 6.7 Hz, 2H), 1.46 (d, J=21.5 Hz, 6H).
¹³C NMR (100 MHz, CDCl₃) δ=163.75, 141.54, 125.95, 114.45, 95.12, 93.47, 64.58 (d, J=5.7 Hz), 40.01 (d, J=22.9 Hz), 27.19 (d, J=24.5 Hz).
¹⁹F NMR (376 MHz, CDCl₃) δ=−137.98−−141.01 (m, 1F).
HRMS: (APCI⁺) [M+H] cal. for $C_{11}H_{15}FNO_3$: 228.1036. found: 228.1030.

¹H NMR (500 MHz, CDCl₃) δ=7.63-7.54 (m, 2H), 7.01-6.90 (m, 2H), 4.18 (t, J=6.7 Hz, 2H), 2.16 (dt, J=19.9, 6.7 Hz, 2H), 1.45 (d, J=21.5 Hz, 6H).
¹³C NMR (100 MHz, CDCl₃) δ=162.04, 134.09, 119.29, 115.26, 104.08, 95.22, 93.57, 64.16 (d, J=5.8 Hz), 40.08 (d, J=22.9 Hz), 27.25 (d, J=24.6 Hz).
¹⁹F NMR (376 MHz, CDCl₃) δ=−137.06−−140.61 (m, 1F).
HRMS: (APCI⁺) [M+H] cal. for $C_{12}H_{15}FNO$: 208.1138. found: 208.1133.

¹H NMR (500 MHz, CDCl₃) δ=9.89 (s, 1H), 7.84 (d, J=8.6 Hz, 2H), 7.01 (d, J=8.7 Hz, 2H), 4.22 (t, J=6.7 Hz, 2H), 2.17 (dt, J=19.8, 6.7 Hz, 2H), 1.46 (d, J=21.5 Hz, 6H).
¹³C NMR (100 MHz, CDCl₃) δ=190.76, 163.62, 131.91, 129.82, 117.64, 95.09, 93.44, 63.95 (d, J=5.8 Hz), 39.95 (d, J=22.9 Hz), 27.05 (d, J=24.6 Hz).
¹⁹F NMR (376 MHz, CDCl₃) δ=−137.84−−140.61 (m, 1F).
HRMS: (APCI⁺) [M+H] cal. for $C_{12}H_{16}FO_2$: 211.1134. found: 211.1129.

The NMR data for the above compounds are in accord with the literature. For example, see LU et al. (2017) "Widely Applicable Hydrofluorination of Alkenes via Bifunctional Activation of Hydrogen Fluoride" J. Am. Chem. Soc., Vol. 139, pp. 18202-18205. NMR spectra can be found in the Supporting Information of LU et al. (2019) "Multifaceted ion exchange resin-supported hydrogen fluoride: a path to flow hydrofluorination" Green Chemistry, Vol. 21, pp. 2224-2228, which is herein incorporated by reference in its entirety.

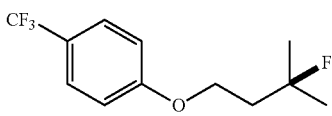

¹H NMR (500 MHz, CDCl₃) δ=7.56 (d, J=8.6 Hz, 2H), 6.97 (d, J=8.6 Hz, 2H), 4.19 (t, J=6.7 Hz, 2H), 2.17 (dt, J=19.8, 6.7 Hz, 2H), 1.46 (d, J=21.5 Hz, 6H).
¹³C NMR (100 MHz, CDCl₃) δ=161.11, 126.92, 126.88, 125.78, 123.06, 122.73, 114.41, 95.26, 93.61, 63.88 (d, J=5.9 Hz), 40.12 (d, J=22.9 Hz), 27.16 (d, J=24.6 Hz).
¹⁹F NMR (376 MHz, CDCl₃) δ=−61.49 (s, 3F), −136.11−−141.04 (m, 1F).
HRMS: (EI⁺) [M] cal. for $C_{12}H_{14}F_4O$: 250.0981. found: 250.0976.

¹H NMR (500 MHz, CDCl₃) δ=7.56 (d, J=8.6 Hz, 1H), 6.64 (dd, J=8.6, 2.0 Hz, 1H), 6.55 (d, J=1.9 Hz, 1H), 4.62 (s, 2H), 4.20 (t, J=6.7 Hz, 2H), 2.17 (dt, J=19.8, 6.7 Hz, 2H), 1.45 (d, J=21.5 Hz, 6H).

$^{13}$C NMR (100 MHz, CDCl$_3$) δ=192.45, 171.39, 162.15, 120.02, 109.29, 106.84, 91.77, 90.01, 88.36, 70.44, 59.37 (d, J=5.7 Hz), 34.84 (d, J=22.9 Hz), 22.07 (d, J=24.5 Hz).

$^{19}$F NMR (376 MHz, CDCl$_3$) δ=−141.82−−146.58 (m, 1F).

HRMS: (APCI$^+$) [M+H] cal. for C$_{13}$H$_{16}$FO$_3$: 239.1083. found: 239.1077.

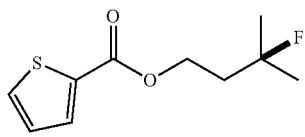
2g $^1$H NMR (500 MHz, CDCl$_3$) δ=7.81 (dd, J=3.7, 1.0 Hz, 1H), 7.56 (dd, J=5.0, 1.1 Hz, 1H), 7.11 (dd, J=4.8, 3.9 Hz, 1H), 4.46 (t, J=6.8 Hz, 2H), 2.11 (dt, J=19.3, 6.8 Hz, 2H), 1.45 (d, J=21.5 Hz, 6H).

$^{13}$C NMR (100 MHz, CDCl$_3$) δ=162.38, 134.02, 133.74, 132.70, 128.06, 95.36, 93.71, 61.36 (d, J=6.4 Hz), 40.10 (d, J=23.2 Hz), 27.38 (d, J=24.6 Hz).

$^{19}$F NMR (376 MHz, CDCl$_3$) δ=−136.80−−139.31 (m, 1F).

HRMS: (EI$^+$) [M] cal. for C$_{10}$H$_{13}$FO$_2$S: 216.0620. found: 216.0613.

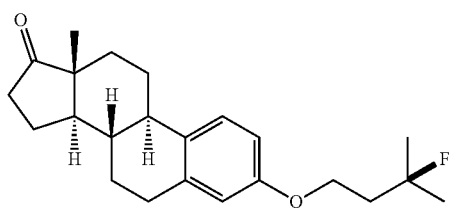
2k $^1$H NMR (500 MHz, CDCl$_3$) δ=7.21 (d, J=8.6 Hz, 1H), 6.73 (dd, J=8.6, 2.6 Hz, 1H), 6.66 (d, J=2.5 Hz, 1H), 4.11 (t, J=6.6 Hz, 2H), 2.96-2.86 (m, 2H), 2.52 (dd, J=19.0, 8.7 Hz, 1H), 2.44-2.37 (m, 1H), 2.26 (dd, J=13.6, 7.2 Hz, 1H), 2.20-1.94 (m, 6H), 1.69-1.40 (m, 13H), 0.92 (s, 3H).

$^{13}$C NMR (100 MHz, CDCl$_3$) δ=220.56, 156.36, 137.44, 131.79, 126.00, 114.15, 111.79, 95.17, 93.54, 63.22, 50.08, 47.67, 43.65, 40.18, 39.96, 38.04, 35.54, 31.25, 29.32, 26.95, 26.70, 26.22, 25.58, 21.25, 13.52.

$^{19}$F NMR (376 MHz, CDCl$_3$) δ=−135.59−−138.79 (m, 1F).

HRMS: (APCI$^+$) [M+H] cal. for C$_{23}$H$_{32}$FO$_2$: 359.2386. found: 359.2383.

5.2 Ring Opening of Aziridines.

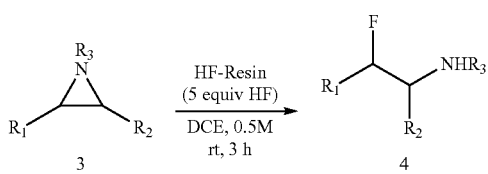

An 8-mL PTFE vial fitted with a stirring bar was charged with dry DCE (0.4 mL) and aziridine starting material (0.2 mmol). HSO$_4$$^-$ A26 Resin-HF (66 mg, 5.0 equiv based on HF) was then added in one portion at room temperature. The progress of the reaction was monitored by TLC (visualized by KMnO$_4$ stain). The reaction was then filtered, and the resin was washed with ethyl acetate (2 mL×2). The filtrate was concentrated, and the residue was purified with flash chromatography.

The NMR data for all of the β-fluoroamine products are in accord with the literature. For example, see OKORO-MOBA et al. 2016 (OKOROMOBA et al. (2016) "Achieving regio- and stereo-control in the fluorination of aziridines under acidic conditions" Chem. Commun., Vol. 52, pp. 13353-13356.). NMR spectra can be found in the Supporting Information of LU et al. (2019) "Multifaceted ion exchange resin-supported hydrogen fluoride: a path to flow hydrofluorination" Green Chemistry, Vol. 21, pp. 2224-2228, which is herein incorporated by reference in its entirety.

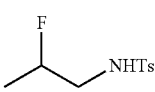
4a

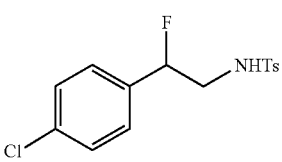
4b

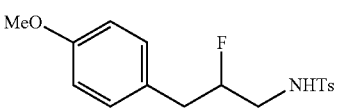
4c

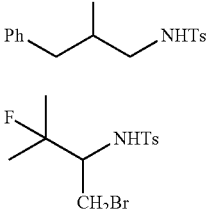
4d

4e

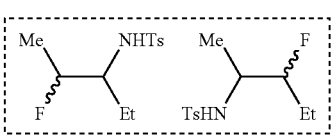
4f

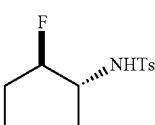
4g

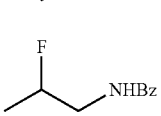
4h

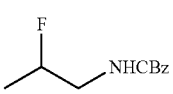
4i

5.3 Fluoro-Prins Reaction

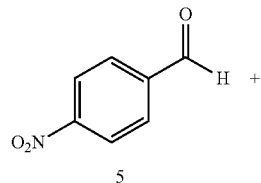

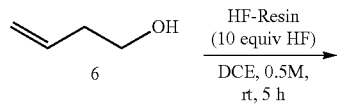

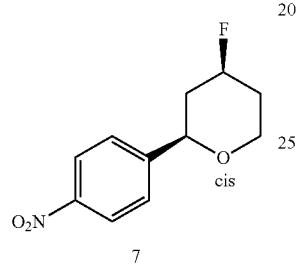

In an 8-mL PTFE vial charged with a magnetic stirring bar, homoallylic alcohol (0.2 mmol) and aldehyde (0.2 mmol) were dissolved in 0.4 mL dichloroethane, then $HSO_4^-$ A26 Resin-HF (133 mg, 10.0 equiv based on HF) was added to the mixture and was stirred for 5 h at room temperature. The progress of the reaction was monitored by TLC (green or dark brown dots on anisaldehyde stain). After completion of the reaction the mixture was quenched with solid $NaHCO_3$, filtered and the filtrate was concentrated. The crude product was chromatographed to afford the corresponding fluoro-tetrahydropyrans.

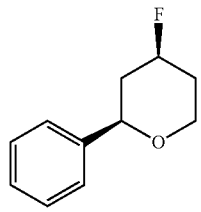

7a

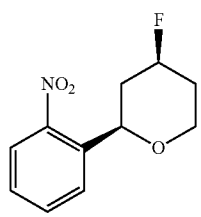

7b

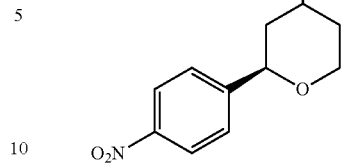

7c

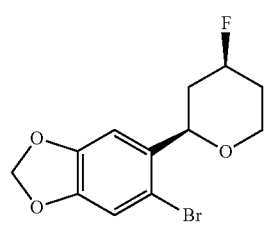

7f

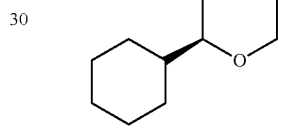

7h

The NMR data for the above products are in accord with the OKOROMOBA et al. (2015) "Preparation of Fluorinated Tetrahydropyrans and Piperidines using a New Nucleophilic Fluorination Reagent DMPU/HF" Org. Lett., Vol. 17, pp. 3975-3977. NMR spectra can be found in the Supporting Information of LU et al. (2019) "Multifaceted ion exchange resin-supported hydrogen fluoride: a path to flow hydrofluorination" Green Chemistry, Vol. 21, pp. 2224-2228, which is herein incorporated by reference in its entirety.

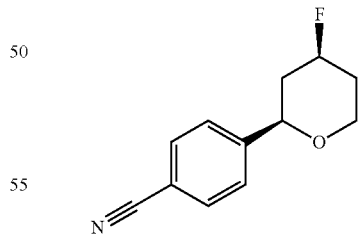

7d $^1$H NMR (500 MHz, $CDCl_3$) δ=7.75 (d, J=8.3 Hz, 2H), 7.56 (d, J=8.1 Hz, 2H), 5.07-4.79 (dm, J=60 Hz, 1H), 4.48 (d, J=11.6 Hz, 1H), 4.39-4.26 (m, 1H), 3.67 (t, J=12.3 Hz, 1H), 2.50-2.38 (m, 1H), 2.30-2.19 (m, 1H), 1.95 (tdd, J=17.5, 12.4, 5.2 Hz, 1H), 1.76 (dt, J=22.6, 11.4 Hz, 1H).

$^{13}$C NMR (100 MHz, $CDCl_3$) δ=146.67, 132.42, 126.46, 118.80, 111.63, 89.80, 88.03, 65.51 (d, J=11.9 Hz), 40.54 (d, J=17.8 Hz), 32.85 (d, J=17.8 Hz).

$^{19}$F NMR (376 MHz, CDCl$_3$) δ=−169.52−−171.77 (m, 1F).

HRMS: (APCI$^+$) [M+H] cal. for C$_{12}$H$_{13}$FNO: 206.0981. found: 206.0976.

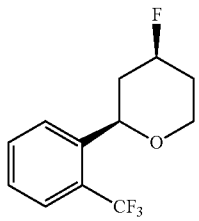

7e $^1$H NMR (500 MHz, CDCl$_3$) δ=7.76 (d, J=7.9 Hz, 1H), 7.61 (dd, J=18.8, 7.9 Hz, 2H), 7.40 (t, J=7.6 Hz, 1H), 4.96-4.72 (m, 1H), 4.68 (d, J=11.2 Hz, 1H), 4.29-4.13 (m, 1H), 3.60 (t, J=12.4 Hz, 1H), 2.43-2.28 (m, 1H), 2.16 (d, J=12.3 Hz, 1H), 2.00-1.79 (m, 1H), 1.68 (dt, J=22.6, 11.3 Hz, 1H).

$^{13}$C NMR (100 MHz, CDCl$_3$) δ=140.21, 132.34, 127.94, 127.77, 126.73, 126.42, 125.61, 125.48, 125.42, 124.77, 122.89, 89.82, 88.05, 73.89, 73.77, 65.57 (d, J=12.1 Hz), 41.17 (d, J=17.4 Hz), 32.94 (d, J=17.8 Hz).

$^{19}$F NMR (376 MHz, CDCl$_3$) δ=−58.50 (s, 3F), −169.88 (dd, J=48.9, 4.6, 1F).

HRMS: (EI$^+$) [M] cal. for C$_{12}$H$_{12}$F$_4$O: 248.0824. found: 248.0819.

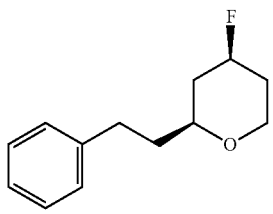

7g $^1$H NMR (500 MHz, CDCl$_3$) δ=7.32 (dd, J=13.8, 6.5 Hz, 1H), 7.24 (m, 3H), 4.67 (dm, J=49.3 Hz, 1H), 4.12 (dt, J=11.4, 5.6 Hz, 1H), 3.40 (t, J=12.2 Hz, 1H), 3.28 (ddd, J=12.4, 4.2, 2.0 Hz, 1H), 2.83 (m, 1H), 2.77-2.67 (m, 1H), 2.17-2.03 (m, 2H), 2.02-1.90 (m, 1H), 1.85-1.73 (m, 2H), 1.58-1.44 (m, 1H).

$^{13}$C NMR (100 MHz, CDCl$_3$) δ=141.82, 128.49, 128.41, 125.88, 90.15, 88.40, 74.69, 74.58, 64.99 (d, J=11.6 Hz), 38.80 (d, J=16.7 Hz), 37.71, 33.15 (d, J=17.4 Hz), 31.65.

$^{19}$F NMR (376 MHz, CDCl$_3$) δ=−169.45 (ddd, J=49.3, 9.8, 4.8, 1F).

HRMS: (EI$^+$) [M] cal. for C$_{13}$H$_{17}$FO: 208.1263. found: 208.1259.

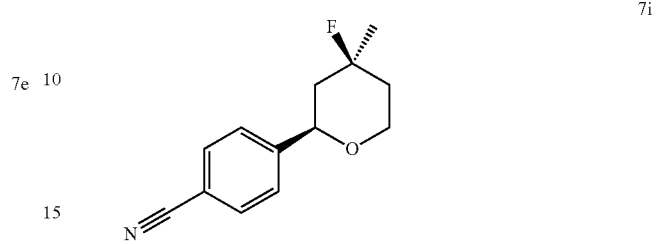

7i $^1$H NMR (500 MHz, CDCl$_3$) δ=7.52 (d, J=8.2 Hz, 1H), 7.35 (d, J=8.1 Hz, 1H), 4.61 (d, J=11.7 Hz, 1H), 4.03-3.89 (m, 1H), 3.81 (td, J=11.9, 4.7 Hz, 1H), 2.02-1.87 (m, 1H), 1.69 (m, 2H), 1.55-1.35 (m, 1H), 1.31 (d, J=21.3 Hz, 2H).

$^{13}$C NMR (100 MHz, CDCl$_3$) δ=147.54, 132.13, 126.18, 118.71, 111.07, 92.70, 91.02, 74.17, 63.74, 44.21 (d, J=21.5 Hz), 35.95 (d, J=21.9 Hz), 27.45 (d, J=24.1 Hz).

$^{19}$F NMR (376 MHz, CDCl$_3$) δ=−151.26−−154.55 (m, 1F).

HRMS: (APCI$^+$) [M+H] cal. for C$_{13}$H$_{15}$FNO: 220.1138. found: 220.1133.

Section 6. Spectral Data of Starting Materials and Products

The spectra data of the starting materials and products can be found in LU et al. (2019) "Multifaceted ion exchange resin-supported hydrogen fluoride: a path to flow hydrofluorination" Green Chemistry, Vol. 21, pp. 2224-2228, which is herein incorporated by reference in its entirety.

Results and Discussion

We examined several types of commercially available anionic resins: Amberlyst A21 has a free amine functional group, whereas Amberlyst A26 and Amberlite IRN78 possess a quaternary ammonium functional group. The commercially available ion exchange resin was treated with a slight excess of aqueous sulfuric acid to substitute the original anion in the resin with HSO$_4$$^−$ (FIG. 1). The modified ion exchange resin was dried and complexed with anhydrous hydrogen fluoride to furnish the ion exchange resin supported HF reagent (for detailed preparation please see above). We tested the reactivity of the ion exchange resin-supported anhydrous hydrogen fluoride reagent using the hydrofluorination of alkene 1a as our model reaction. We found that Amberlyst A26 affixed more hydrogen fluoride per gram of dry resin and showed higher reactivity in the hydrofluorination 1a than the other two resin-HF complexes (Table 1, entry 4 vs entries 1, 2). To better understand the use of bisulfate in the polymeric HF complex, we tested another ion exchange resin, Amberlite IR-120 Na$^+$, bearing an SO$_3$$^−$Na$^+$ functionality. The resulting complex showed a lower reactivity than the A-26 resin HF complex because of its weaker acidity (Table 1, entry 3 vs entry 4). Solvent optimization indicated that dichloroethane (DCE) provided a higher yield (Table 1, entries 4, 7-14). Further optimization demonstrated that 15 equivalents of HF (Table 1, entries 4-6) and a reaction time of 15 h provided a higher yield (Table 1, entry 15).

TABLE 1

Reaction condition optimization for hydrofluorination of alkene.

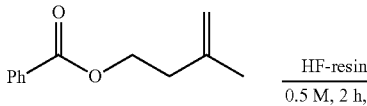

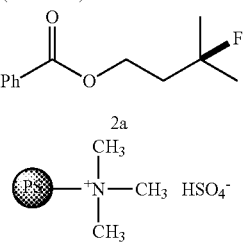

HSO₄⁻ A26 resin
Size: 560-700 μm
capacity: 0.8 meq/mL

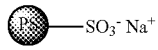

Na⁺ IR-120 resin

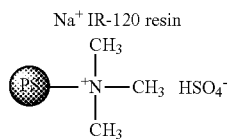

HSO₄⁻ IRN78 resin
Size: 580-680 μm
capacity: 1.1 meq/mL

| entry | resin - HF (wt/wt%) | HF equiv | solvent | yield (%)[a] |
|---|---|---|---|---|
| 1 | HSO₄⁻ A21 resin- HF (30%) | 10 | DCE | 19 |
| 2 | HSO₄⁻ IRN78 resin- HF (28%) | 10 | DCE | 23 |
| 3 | IR-120-Na⁺ resin - HF (23%) | 10 | DCE | 0 |
| 4 | HSO₄⁻A26 resin - HF (30%) | 10 | DCE | 28 |
| 5 | HSO₄⁻ A26 resin - HF (30%) | 15 | DCE | 58 |
| 6 | HSO₄⁻ A26 resin - HF (30%) | 5 | DCE | 7 |
| 7 | HSO₄⁻ A26 resin - HF (30%) | 10 | CH₃CN | 0 |
| 8 | HSO₄⁻ A26 resin - HF (30%) | 10 | DCM | 22 |
| 9 | HSO₄⁻ A26 resin - HF (30%) | 10 | Dioxane | 0 |
| 10 | HSO₄⁻ A26 resin - HF (30%) | 10 | DMF | 0 |
| 11 | HSO₄⁻ A26 resin - HF (30%) | 10 | DMSO | 0 |
| 12 | HSO₄⁻ A26 resin - HF (30%) | 10 | Et₂O | 0 |
| 13 | HSO₄⁻ A26 resin - HF (30%) | 10 | EtOAc | 0 |
| 14 | HSO₄⁻ A26 resin - HF (30%) | 10 | Toluene | 51 |
| 15[b] | HSO₄⁻ A26 resin - HF (30%) | 15 | DCE | 87 |

[a]NMR yield with benzotrifluoride as internal standard;
[b]15 hours.

Having found a reaction protocol in the hydrofluorination of alkenes, we explored the substrate scope and functional group tolerance. As shown in Table 2, disubstituted and trisubstituted alkenes showed good to excellent yield. The tested monosubstituted alkenes appeared to be unreactive (data not shown). A wide range of functional groups such as esters (2a, 2g, 2h, 2n, 2p), ethers (2b-2f), nitro (2c), nitrile (2d), aldehyde (2e), ketones (2f, 2k, 2m), alcohols (2l, 2o) were well tolerated. Acceptable to very good yields were obtained with different heterocyclic substrates like thiophene (2g), pyridine (2h), indazole (2i) and benzotriazole (2j). Longer reaction times were typically needed for substrates containing basic moieties (2h, 2i, 2j). Since alkenes are commonly found in natural products, we screened an estrone-tethered disubstituted alkene, which furnished a 67% yield of the product (2k). We found that a natural product with a secondary alcohol, such as (−)-dihydrocarveol (2l), gave only a 52% yield of the product whereas nootkatone, possessing an α, β-unsaturated ketone group (2m), gave an 84% yield. The hydrofluorination of (−)-β-citronellol, which bears a primary alcohol functionality, gave a 79% yield of the product 2o. And we found that the cyclopropane motif remained intact after the reaction of ethyl chrysanthemate with HF (2p).

The synthesis of β-fluoroamines via ring-opening of aziridines with HF is, in principle, an ideal preparation method because of the low cost of reagents, mild reaction conditions and general accessibility of substrates, but the production of regioisomers and stereoisomers has muddled the efficiency of this strategy. Using our modified ion exchange resin supported HF (resin A26-HF), we achieved many useful characteristics including but not limited to high selectivity, good functional group tolerance, avoidance of the introduction of impurities to the reaction mixture, and simplified the workup procedure (e.g., only filtration was typically needed).

TABLE 2

Hydrofluorination of alkenes.[a]

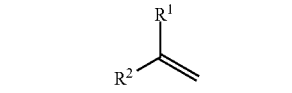

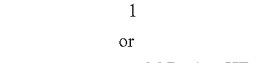

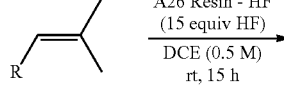

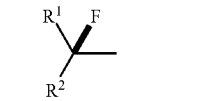

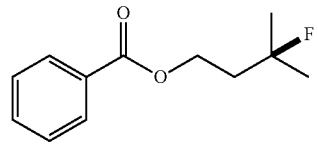

2a, 87%

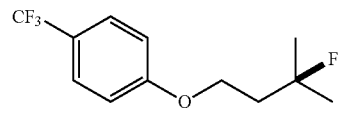

2b, 73%

TABLE 2-continued

Hydrofluorination of alkenes.[a]

2c, 85%

2d, 84%

2e, 82%

2f, 75%

2g, 64%

2h, 85%, (48 h)

2i, 53%, (72 h)

2j, 56%, (72 h)

2k, 67%

2l, 52%

2m, 84%
Fluoro-(+)-Nootkatone 2n, 82%

2o, 79%
Fluoro-(−)-β–Citronellol 2p, 57%
Fluoro-ethyl chrysanthemate

[a]Reaction conditions: 1 (0.2 mmol), A26 Resin - HF(15 equiv HF), DCE (0.4 mL), room temperature, 15h. All yields are for the isolated product.

As shown in the Table 3, hydrofluorination of the mono alkyl-, aryl-, and benzyl-substituted N-tosylaziridines (3a-3d) occurred at the most substituted carbon and delivered primary alkyl amines (4a-4d) in 62%-83% yields. The trisubstituted aziridine 3f was fluorinated at the more substituted carbon in 61% yield. When 2-ethyl-3-methyl-1-tosylaziridine was the substrate, an inseparable mixture of regioisomers and diastereomers was generated (40. A bicyclic aziridine was also tested and converted to trans-β- fluoroamine 4g in good yield and diastereoselectivity. Various N-protecting groups such as tosyl (4a-4g), benzoyl (4h), and Cbz (carboxybenzyl) (4i) were well tolerated under the reaction conditions, affording the corresponding products in the shown yields and regioselectivity.

TABLE 3

Ring-opening of aziridines 3.[a]

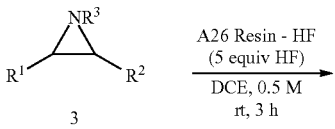

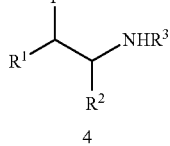

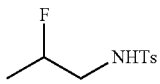

4a, 62%
(14:1)[b]

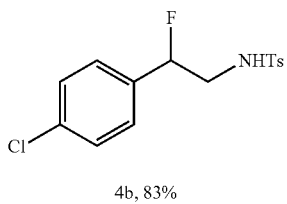

4b, 83%

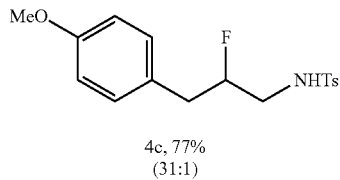

4c, 77%
(31:1)

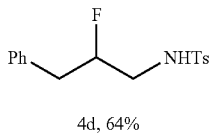

4d, 64%

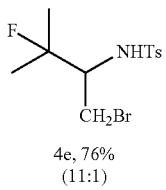

4e, 76%
(11:1)

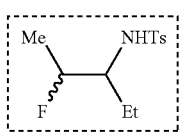

4f, 61%[c]
(11:6:3:1)

TABLE 3-continued

Ring-opening of aziridines 3.[a]

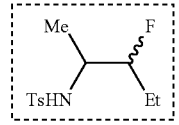

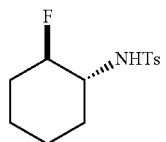

4g, 63%

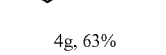

4h, 95%
(31:1)

4i, 74%
(40:1)

[a] Reaction conditions: 3 (0.2 mmol), A26 Resin - HF (5 equiv HF), DCE (0.4 mL), room temperature, 3h. All yields are for the isolated product.
[b] Numbers in parenthesis are regioisomeric ratio determined by $^{19}$F NMR.
[c] starting aziridine are mixture of cis- and trans-isomers.

With our ion exchange resin supported-HF reagent, we obtained fluorinated tetrahydropyrans with properties including but not limited to high diastereoselectivities and good yields. As illustrated in Table 3, both aromatic (7a-7f) and aliphatic aldehydes (7g, 7h) gave the indicated yields of the corresponding products.

TABLE 4

Fluoro-Prins reaction.[a]

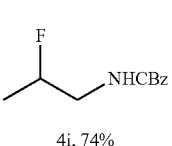

TABLE 4-continued

Fluoro-Prins reaction.[a]

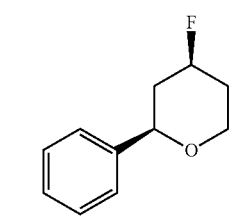

7a, 89%

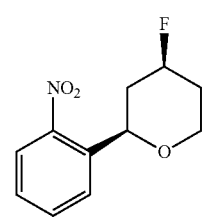

7b, 69%

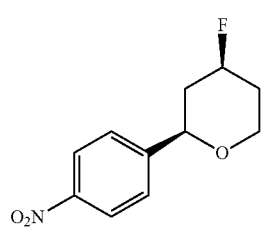

7c, 82%

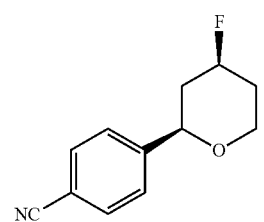

7d, 71%
(cis:trans = 53:1)

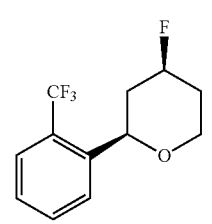

7e, 65%

TABLE 4-continued

Fluoro-Prins reaction.[a]

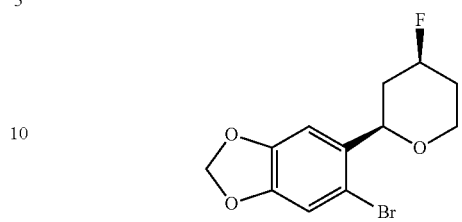

7f, 51%

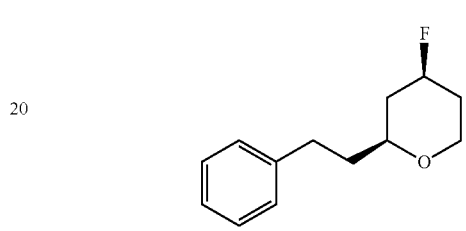

7g, 71%

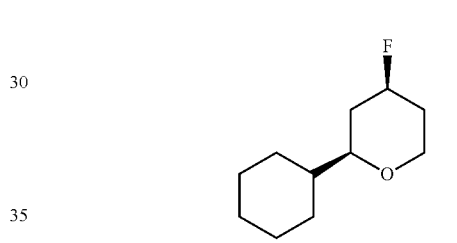

7h, 73%

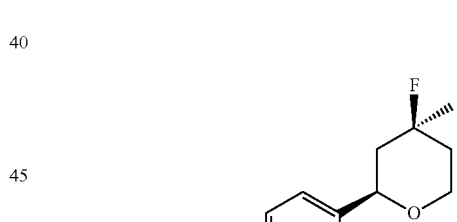

7i, 74%

[a]Reaction conditions: 5 (0.2 mmol), 6 (0.2 mmol), A26 Resin - HF(10 equiv HF), DCE (0.4 mL), room temperature, 5 h. All yields are for the isolated product Electron-poor aldehyde substrates (7b-7e) gave higher yields than electron rich aldehydes (7f). Notably, a disubstituted fluorinated tetrahydropyran could be synthesized with good yield and diastereoselectivity when isoprenol was used as substrate (7i). Next, we compared the reactivity of our polymer supported HF reagent with the only commercially available polymeric hydrogen fluoride reagent—poly-4-vinylpyridium poly(hydrogen fluoride) (PVP-HF) (equations A, B and C). Our reagent showed better efficiency in all three reactions. It should be noted that our ion exchange resin is less costly than PVP, making it suitable for larger scale synthesis.

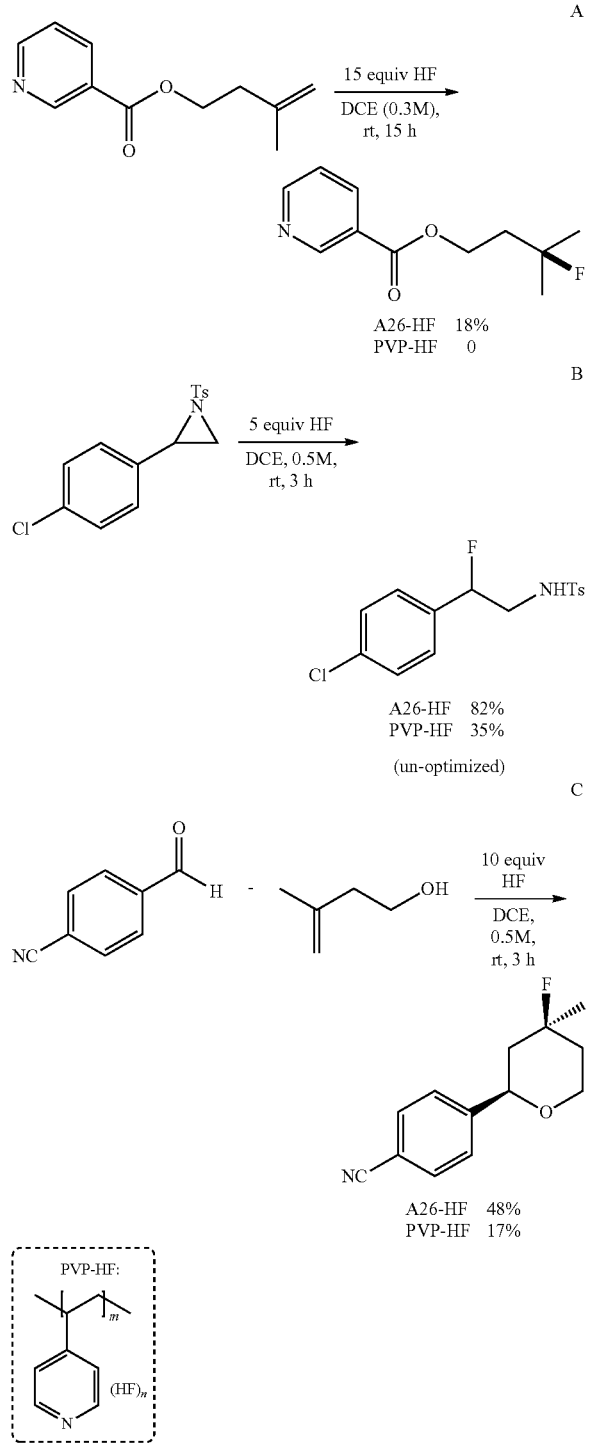

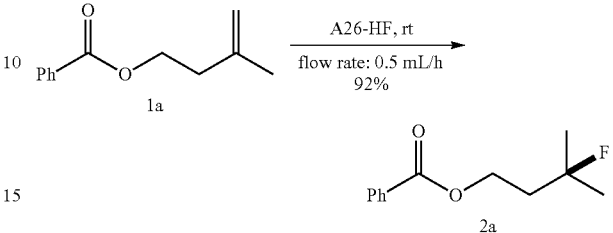

avoid etching the glassware. The eluent was collected and concentrated to afford the crude product in 92% NMR yield. This flow reactor could be used for large scale synthesis. In addition, if desired, the ion exchange resin could be recycled to complex with more HF and reused.

Figure 3:
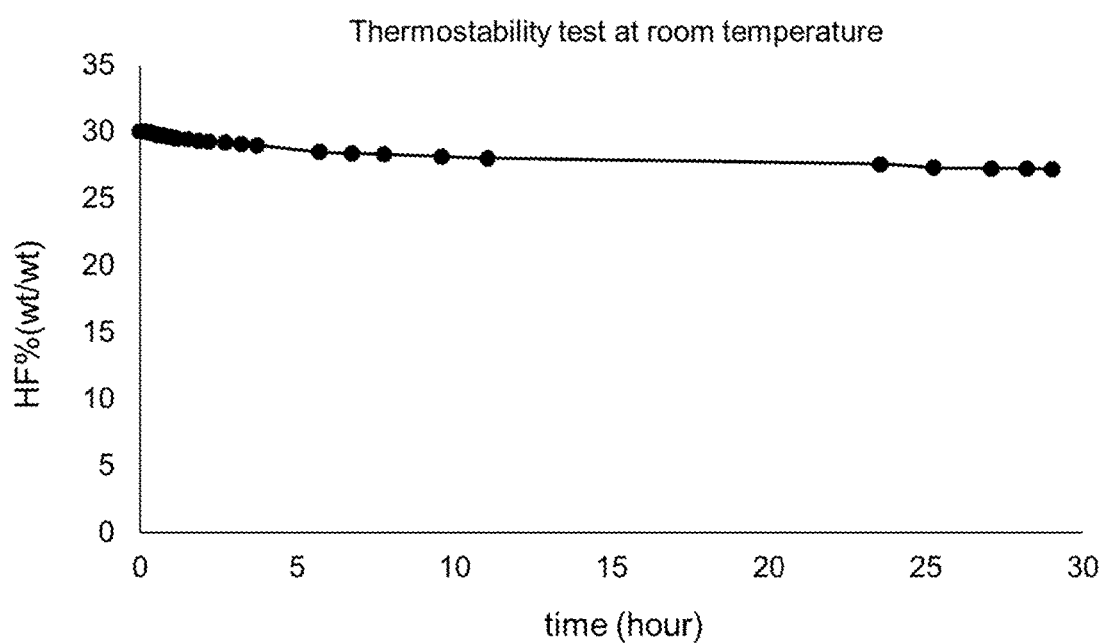
FIG. 3: Thermostability test of polymer supported HF reagent by measuring loss of HF in open air. (A) Thermostability test of polymer supported HF reagent at room temperature. (B) Thermostability test of polymer supported HF reagent at 50° C.
Figure 3:
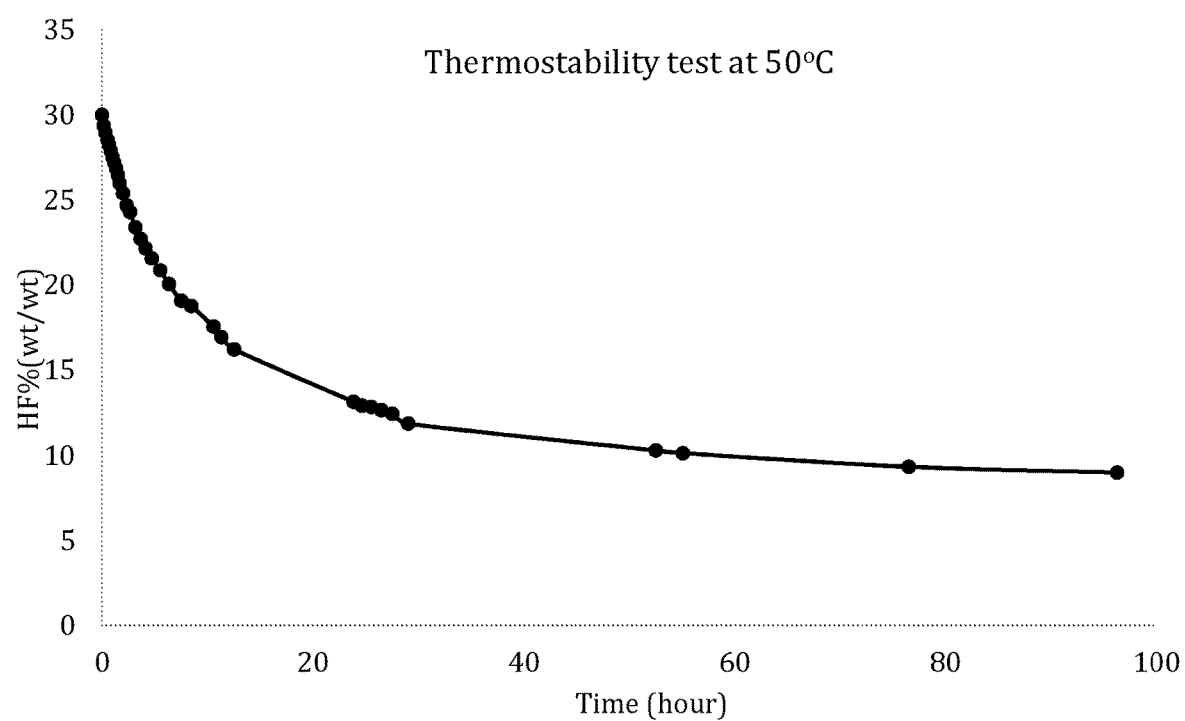

The thermal stability of the polymeric HF reagent (resin A26-HF) was also investigated (FIG. 3A). We found only a 2 wt % HF loss when an open vial containing the resin was placed in a well vented fume hood for 30 h. The stability of this reagent should facilitate its packing, transportation and storage (see above).

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

Figure 5:
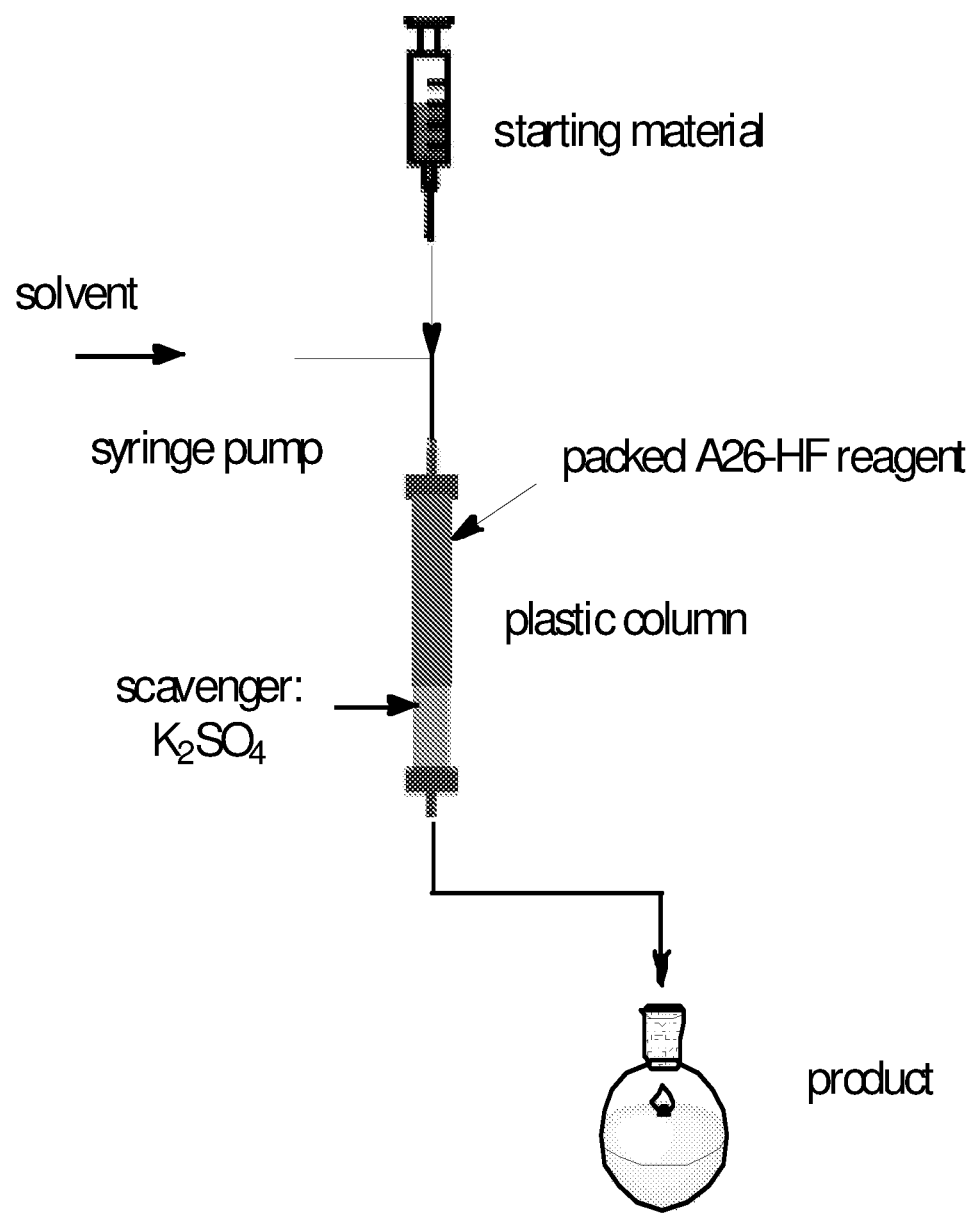
FIG. 5: Use of polymer supported HF reagent in flow reaction.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodi- As mentioned above, the use of HF based reagents under flow conditions has not been reported. Our ionic exchange resin-supported HF reagent could be easily packed into a plastic tube or a column suitable for flow reactions (see above). We used the hydrofluorination of alkene 1a to test the flow conditions at room temperature (FIG. 5). A solution of alkene was injected into the packed column and the column was flushed with neat solvent (DCE) at 0.5 mL/h flow rate. We used an HF-scavenger at the bottom of column to prevent excess HF from entering the eluent stream and to ments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner Indeed, various modifications of the invention in addition to those described herein will become apparent to those skilled in the art from the foregoing description and the accompanying figures. Such modifications are intended to fall within the scope of the appended claims.

What is claimed is:

1. A catalyst selected from Formula (I)

$$\text{resin-anion-}x\text{HF} \tag{I}$$

wherein resin is an anion exchange resin, anion is $HSO_4^-$, $BzO^-$, $AcO^-$, $H_2PO_4^-$, $HPO_4^{2-}$, $PO_4^{3-}$, $MeSO_3^-$, $NO_3^-$, $ReO_4^-$, $CF_3SO_3^-$, $ClO_4^-$, or $CF_3(CF_2)_3SO_3^-$, x is 1, 2, 3, 4, 5, 6, 7, 8, 9, 10, 11, 12, 13, 14, 15, 16, 17, 18, 19, 20, 21, 22, 23, 24, or 25, and x is the number of equivalents of HF per equivalent anion in the resin-anion.

2. The catalyst of claim 1, wherein the resin comprises a secondary ammonium group, a tertiary ammonium group, or a quaternary ammonium group.

3. The catalyst of claim 1, wherein x is 5, 6, 7, 8, 9, 10, 11, 12, 13, 14, 15, 16, 17, 18, 19, or 20.

4. The catalyst of claim 1, wherein x is 5, 10, or 15.

5. The catalyst of claim 1, wherein the anion is $HSO_4^-$, $BzO^-$, $AcO^-$, $H_2PO_4^-$, $HPO_4^{2-}$, or $PO_4^{3-}$.

6. The catalyst of claim 1, wherein the anion is $HSO_4^-$.

7. The catalyst of claim 1, wherein (1) the catalyst is resin-$HSO_4^-$-5HF, resin-$HSO_4^-$-10HF, or resin-$HSO_4^-$-15HF, (2) the resin comprises a quaternary ammonium group or trimethylammonium, or (3) both.

8. A composition comprising the catalyst of claim 1, and a solvent.

9. The composition of claim 8, wherein the solvent is DCM (dichloromethane), DCE (1,2 dichloroethane), dioxane, $Et_2O$ (diethylether), $CH_3CN$, EtOAc (ethyl acetate), DMSO (dimethyl sulfoxide), DMF (dimethyl formamide), or toluene.

10. The composition of claim 8, wherein the solvent is DCM, DCE, or toluene.

11. A method for hydrofluorination of a reactant organic compound, the method comprising contacting a composition comprising the reactant organic compound with a composition comprising a catalyst of Formula (I) of claim 1, wherein the reactant organic compound is (1) an organic compound comprising one or more alkenes or (2) an organic compound comprising an aziridine, the composition comprising the reactant organic compound optionally comprises a solvent, the composition comprising the catalyst of Formula (I) optionally comprises a solvent, or both, and the solvent optionally in each composition can be the same or different.

12. The method of claim 11, wherein the composition comprising the reactant organic compound comprises a solvent, the composition comprising a catalyst of Formula (I) comprises a solvent, or both; and the solvent is the same in each composition.

13. The method of claim 11, wherein the reactant organic compound comprises one or more alkenes and the composition comprising the reactant organic compound further comprises a reactant aldehyde.

14. The method of claim 11, wherein the method comprises (a) providing a composition comprising the solvent and the organic compound comprising one or more alkenes; and (b) contacting the composition of (a) with a composition comprising the catalyst of Formula (I), wherein the product molecule comprises one F on one of the carbons where an alkene was in the organic compound comprising one or more alkenes.

15. The method of claim 11, wherein the composition comprising the reactant organic compound further comprises a reactant aldehyde and the product molecule comprises a cyclization with the reactant aldehyde.

16. The method of claim 11, wherein the method comprises (a) providing a composition comprising the solvent and the organic compound comprising an aziridine; and (b) contacting the composition of (a) with a composition comprising the catalyst of Formula (I), wherein the product molecule comprises an opened aziridine ring and an F added to one of the two aziridine ring carbons.

17. The method of claim 11, wherein the contacting in step (b) comprises (i) mixing the composition of (a) with the composition comprising the catalyst of Formula (I) or (ii) moving the composition of (a) through a column with the composition comprising a catalyst of Formula (I).

18. The method of claim 11, wherein the composition comprising the catalyst further comprises a solvent which may be the same or different as the solvent in step (a).

19. The method of claim 11, wherein the solvent in step (a), step (b) or both is DCE.

20. The method of claim 11, wherein the catalyst is resin-anion-xHF and x is 5, 10, or 15.

21. The method of claim 11, wherein (1) the catalyst is resin-$HSO_4^-$-5HF, resin-$HSO_4^-$-10HF, or resin —$HSO_4^-$-15HF, (2) the resin comprises a quaternary ammonium group or trimethylammonium, or (3) both.

22. The method of claim 11, wherein the amount of the reactant organic molecule is at least about 0.01 mmol.

23. The method of claim 11, wherein the contacting occurs for at least about 0.01 hours.

24. The method of claim 11, wherein the contacting occurs for from about 5 hours to about 100 hours.

25. The method of claim 11, wherein the temperature during the contacting is at least about 15° C.

26. The method of claim 11, wherein the molecular weight of the reactant organic compound, the reactant aldehyde, or both is no more than about 3,000 daltons.

27. A method for preparing the catalyst of claim 1 comprising (a) optionally contacting the resin with the anion or a salt of the anion to produce resin-anion and (b) contacting HF with resin-anion.

28. The method of claim 27, wherein the contacting in step (b) is at a temperature of no more than about 20° C.

29. The method of claim 27, wherein the mole ratio of HF to anion (in the resin-anion) is at least about 5.

* * * * *